United States Patent
Koyama et al.

(10) Patent No.: US 6,355,642 B1
(45) Date of Patent: Mar. 12, 2002

(54) TETRAHYDROBENZINDOLE COMPOUNDS

(75) Inventors: Masao Koyama; Chika Kikuchi; Osamu Ushiroda; Takashi Ando; Hiroshi Nagaso; Kazuyuki Fuji; Masayo Okuno; Toyokazu Hiranuma, all of Kanagawa (JP)

(73) Assignee: Meiji Seika Kaisha, Ltd., Tokyo (JP)

(*) Notice: Subject to any disclaimer, the term of this patent is extended or adjusted under 35 U.S.C. 154(b) by 0 days.

(21) Appl. No.: 09/214,114

(22) PCT Filed: Jun. 27, 1997

(86) PCT No.: PCT/JP97/02226

§ 371 Date: Dec. 28, 1998

§ 102(e) Date: Dec. 28, 1998

(87) PCT Pub. No.: WO98/00400

PCT Pub. Date: Jan. 8, 1998

(30) Foreign Application Priority Data

| Jun. 28, 1996 | (JP) | 8-169702 |
| Apr. 15, 1997 | (JP) | 9-096271 |
| May 21, 1997 | (JP) | 9-130201 |
| Jun. 3, 1997 | (JP) | 9-144376 |

(51) Int. Cl.$^7$ .................. A61K 31/40; A61P 25/18; C07D 209/92; C07D 401/06; C07D 403/14
(52) U.S. Cl. .................. 514/252.19; 514/253.09; 514/254.08; 514/323; 514/339; 514/411; 544/295; 544/364; 544/372; 546/200; 546/276.7; 548/437
(58) Field of Search .................. 544/295, 364, 544/372; 546/200, 276.7; 548/437; 514/252.19, 253.09, 254.08, 323, 339, 411, 252, 253, 254

(56) References Cited

FOREIGN PATENT DOCUMENTS

| EP | 429 341 A2 | 5/1991 |
| EP | 433 149 A | 6/1991 |
| EP | 0 464 604 A | 1/1992 |
| JP | 3-190858 | 8/1991 |
| JP | 4-230377 | 8/1992 |

OTHER PUBLICATIONS

International Search Report.
Malleron J.–L et al. "Napthosultam Derivatives: A new class of potent and selective 5–HT2antagonists" Journal of Medicinal Chemistry, US, American Chemical Society, Washington, vol. 34, No. 8, 1991, pp. 2477–2483, XP000579809 ISSN:0022–2623.

Malleron J–L et al., "New indole derivatives as potent and selective serotonin uptake inhibitors" Journal of Medicinal Chemistry, US American Chemical Society, Washington, vol. 36, No. 9, 1993, pp. 1194–1202, XP00019590 ISSN: 0022–2623.

Roth B L et al. "Binding of Typical and Atypical Antipsychotic Agents to 5–Hydroxytryptamine–6 and 5–Hydroxytryptamine–7 Receptors" J. Pharmacol. Exp. Ther., vol. 268, No. 3, 1994, pp. 1403–1410 XP002152648 Baltimore.

Eglen R.M., et al. "The 5–HT7 receptor: orphan found" Trends in Pharmacological Sciences, GB, Elsevier Trends Journal, Cambridge, vol. 18, No. 4, pp. 104–107 XP004058670 ISSN: 0165–6147, 1997.

Hoyer D. and Martin G.: "5–HT receptor classification and nomenclature: towards a harmonization with the human genome" Neuropharmacology, GB, Pergamon Press, Oxford, No. 36, Apr. 1, 1997, pp. 419–428, XP002075372 ISSN: 0028–3908.

Saudou F. et al., "5–HT receptor subtypes: Molecular and Funcitional Diversity" Medicinal Chemistry Research, US, Birkhaeuser, Boston, vol. 4, No. 1, pp. 16–84 XP000604196 ISSN: 1054–2523, 1994.

Kikuchi, C., et al. "Tetrahydrobenzindoles: Selective Antagonists of the 5–HT7 Receptor" Journal Med. Chem., vol. 42, 1999, pp. 533–535, XP002152460 Washington.

*Primary Examiner*—Brenda Coleman
(74) *Attorney, Agent, or Firm*—Sughrue, Mion, Zinn, Macpeak & Seas, PLLC

(57) ABSTRACT

A compound of formula (I) for use in the treatment or prevention of mental diseases

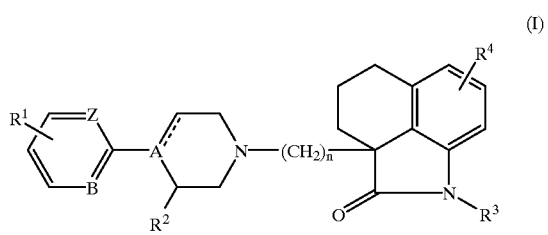

A is N, CH, C having a double bond or $CR^5$; each of B and Z is independently N, CH or $CR^1$, with the proviso that A is N when B and/or Z is N; $R^1$, $R^2$, $R^3$, $R^4$ and $R^5$ and n are as defined in the specification.

11 Claims, No Drawings

TETRAHYDROBENZINDOLE COMPOUNDS

This is the U.S. national stage application under 35 U.S.C. § 371 of PCT/JP97/02226, filed Jun. 27, 1997.

TECHNICAL FIELD

This invention relates to a tetrahydrobenzindole compound. Since this tetrahydrobenzindole compound binds to serotonin receptors in the living body, it also relates to the treatment and prevention of diseases which are induced by the abnormality of serotonin controlling functions, such as manic-depressive psychosis, anxiety, schizophrenia, sleep disorders, jet lag, gastrointestinal disease, cardiovascular disease and the like.

BACKGROUND ART

In the present society, the environment which surrounds us is sharply changing, and adaptation for it is becoming more and more difficult. Thus, a part which is too much for adaptation for the social environment is accumulated in our bodies as stress and sometimes causes abnormality of not only physical functions but also mental functions. In the treatment of abnormal mental functions, importance of drug therapy has been increasing more and more in addition to psychological therapy, so that development of effective drugs has been put forward.

Since the indication about the action of serotonin (5-HT) in the central nervous system, classification and distribution of serotonin receptors have been revealed gradually. By the detailed analysis of serotonin receptors using molecular biological technique in recent years, $5\text{-}HT_1$ and its subtypes, $5\text{-}HT_2$ and its subtypes, $5\text{-}HT_3$, $5\text{-}HT_4$, $5\text{-}HT_6$, $5\text{-}HT_7$ and the like have been specified and a total of 14 different serotonin receptors have been proposed [R. D. Ward et al., Neuroscience, Vol. 64, pp. 1105–1111 (1995)]. Studies on the physiological functions of serotonin receptors have also been making progress, and not only their relation to appetite, body temperature regulation, blood pressure regulation and the like body functions but also their relation to depression, anxiety, schizophrenia, sleep disorders and the like mental functions have been revealed [P. L. Bonate et al., Clinical Neuropharmacology, 14, pp. 1–16 (1991)]. Actually, $5\text{-}HT_{1A}$ receptor agonists, $5\text{-}HT_2$ receptor inhibitors and 5-HT re-uptake inhibitors are now used in the clinical field.

It has been reported also that, since serotonin receptor $5\text{-}HT_6$ has the affinity particularly for a drug group classified as atypical among already known schizophrenia treating drugs, the serotonin receptor $5\text{-}HT_6$ is closely related to the efficacy of these drugs [R. D. Ward et al., Neuroscience, Vol. 64, pp. 1105–1111 (1995)].

Roth B. L. et al. [J. Pharmacol. Exp. Ther., 1994, 268 (3), 163–170] have reported that several atypical schizophrenia treating drugs including clozapine have strong affinity for the $5HT_6$ receptor, and several typical schizophrenia treating drugs show high affinity for both of the $5HT_6$ and $5HT_7$ receptors.

Also, Tollefson G. D. et al [Psychopharmacol. Bull., 1991, 27, 163–170] have reported that a $5HT_{1A}$ partial agonist, buspirone, has high therapeutic effect for patients having both symptoms of depression and anxiety.

In addition, L. M. Caster et al. [J. Med. Chem., Vol. 38, 4760–4763 (1994)] have reported that certain N-butylpiperidines inhibit serotonin receptor $5\text{-}HT_4$ selectively and are useful for the treatment of irritable digestive organ syndrome, and T. W. Lovenberg et al. [Neuron, Vol. 11, 449–458 (1993)] have assumed that serotonin receptor $5\text{-}HT_7$ exerts an important function in the human circadian rhythm regulation.

As has been described in the above, functions of serotonin receptors are being revealed, so that great concern is directed toward the creation of a chemical substance which exerts its function upon one of these serotonin receptors or simultaneously upon a plurality of these serotonin receptors, because it will provide pharmaceutical preparations which are useful not only for the physiological studies on the function of central and peripheral nervous systems but also for the treatment and prevention of various diseases which are considered to be induced by the abnormality of intracerebral and peripheral serotonin controlling functions, such as schizophrenia, manic-depressive psychosis, anxiety, sleep disorders, jet lag, gastrointestinal disease, migraine and abnormal blood pressure and the like cardiovascular disease.

DISCLOSURE OF THE INVENTION

The present invention comprises the following constructions.

1. A compound represented by formula (I):

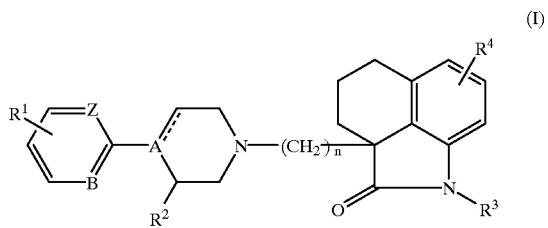

[wherein A represents N, CH, C having a double bond or $CR^5$; each of B and Z independently represents N or $CR^1$, with the proviso that A is N when B and/or Z is N; $R^1$ represents a hydrogen atom, a halogen atom, a lower alkyl group, a cyano group, a trihalomethyl group, a hydroxy group, an alkoxy group, an alkylthio group, an alkylsulfinyl group, an alkylsulfonyl group, an alkoxycarbonyl group, a sulfamoyl group, an amino group, a substituted amino group, a carbamoyl group, an alkylcarbamoyl group, an acyl group or a carboxy group; $R^2$ represents a hydrogen atom or a lower alkyl group; $R^3$ represents a hydrogen atom, a lower alkyl group or an aralkyl group; $R^4$ represents a hydrogen atom, a halogen atom, a lower alkyl group, a hydroxy group, an alkoxy group, an acyl group, an alkoxycarbonyl group, a nitro group, an amino group, a substituted amino group, a carbamoyl group, an alkylcarbamoyl group or an acyloxy group; $R^5$ represents a lower alkyl group, a cyano group, a carbamoyl group, a carboxy group, an acyl group, an acyloxy group, an alkoxy group, an alkoxycarbonyl group, a trihalomethyl group or a hydroxy group; and n is an integer of 2 to 6] or a pharmaceutically acceptable salt thereof.

2. A compound according to the aforementioned item 1, which is represented by formula (II):

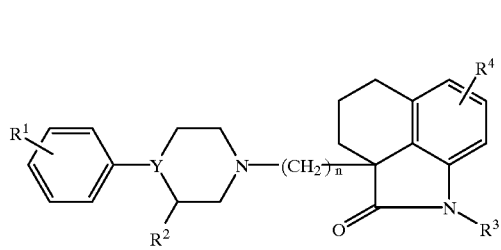

(II)

[wherein Y represents N or CH; and $R^1$, $R^2$, $R^3$, $R^4$ and n are as defined in the foregoing] or a pharmaceutically acceptable salt thereof.

3. A compound according to the aforementioned item 1, which is represented by formula (III):

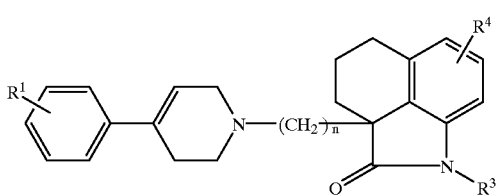

(III)

[wherein $R^1$, $R^3$, $R^4$ and n are as defined in the foregoing] or a pharmaceutically acceptable salt thereof.

4. A compound according to the aforementioned item 1, which is represented by formula (IV):

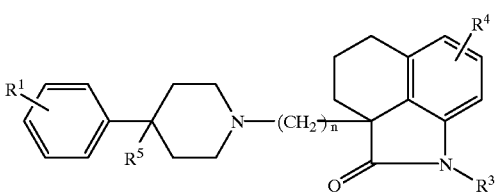

(IV)

[wherein $R^1$, $R^2$, $R^3$, $R^4$, $R^5$ and n are as defined in the foregoing] or a pharmaceutically acceptable salt thereof.

5. A compound according to the aforementioned item 1, which is represented by formula (V):

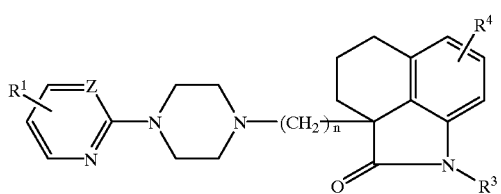

(V)

[wherein $R^1$, $R^3$, $R^4$, Z and n are as defined in the foregoing; and $R^1$ is preferably a hydrogen atom, a lower alkyl group, a trihalomethyl group or an alkoxy group] or a pharmaceutically acceptable salt thereof.

6. A compound represented by formula (a-1):

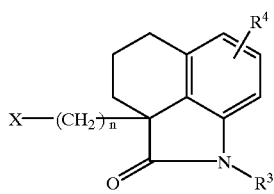

(a-1)

[wherein X represents a halogen atom, a methanesulfonyloxy, ethanesulfonyloxy or the like alkylsulfonic acid ester residue or a benzenesulfonyloxy group, p-toluenesulfonyloxy or the like arylsulfonic acid ester residue; and $R^3$, $R^4$ and n are as defined in the foregoing].

7. A pharmaceutical composition for use in the treatment or prevention of mental diseases, which contains any one of the compounds of the aforementioned items 1 to 5 or a pharmaceutically acceptable salt thereof.

The compounds which are provided by the present invention can be produced by the chemical synthesis methods described below. In the following descriptions concerning the chemical substances of the present invention and production methods thereof, the term "halogen atom" means fluorine, chlorine, bromine or iodine atom, the term "lower alkyl" means a methyl, ethyl or the like straight chain alkyl group having 1 to 4 carbon atoms, an isopropyl, isobutyl, t-butyl or the like branched-chain alkyl group or their halogen-substituted alkyl group, and the term "base to be used as a catalyst" means sodium hydroxide, potassium carbonate, triethylamine or the like.

In the formula (I), $R^1$ represents a hydrogen atom, a halogen atom, a lower alkyl group, a cyano group, a trihalomethyl group (wherein the three halogen atoms are as defined in the foregoing and may be the same or different from one another, and a trifluoromethyl group is preferred), a hydroxy group, an alkoxy (preferably having 1 to 4 carbon atoms, such as methoxy and ethoxy), an alkylthio group (preferably having 1 to 4 carbon atoms, such as methylthio and ethylthio), a alkylsulfinyl group (preferably having 1 to 4 carbon atoms), an alkylsulfonyl group (preferably having 1 to 4 carbon atoms), an alkoxycarbonyl group (preferably having 1 to 4 carbon atoms), a sulfamoyl group, an amino group, a substituted amino group (preferably an amino substituted with a lower alkyl, such as dimethylamino and diethylamino), a carbamoyl group, an alkylcarbamoyl group (preferably the alkyl moiety is a lower alkyl, such as dimethylcarbamoyl), an acyl group (preferably having 1 to 4 carbon atoms, such as acetyl) or a carboxy group; $R^2$ represents a hydrogen atom or a lower alkyl group; $R^3$ represents a hydrogen atom, a lower alkyl group or an aralkyl group (such as benzyl); $R^4$ represents a hydrogen atom, a halogen atom, a lower alkyl group, a hydroxy group, an alkoxy group (preferably having 1 to 4 carbon atoms, such as methoxy and ethoxy), an acyl group (preferably having 1 to 4 carbon atoms, such as acetyl), an alkoxycarbonyl group (preferably having 1 to 4 carbon atoms, such as methoxycarbonyl and ethoxycarbonyl), a nitro group, an amino group, a substituted amino group (preferably an amino substituted with a lower alkyl, such as dimethylamino and diethylamino), a carbamoyl group, an alkylcarbamoyl group (preferably the alkyl moiety is a lower alkyl, such as dimethylcarbamoyl) or an acyloxy group (preferably having 1 to 4 carbon atoms, such as acetoxy); and $R^5$ represents a lower alkyl group, a cyano group, a carbamoyl group, a carboxy group, an acyl group (preferably having 1 to 4 carbon atoms, such as acetyl), an acyloxy group (preferably having 1 to 4 carbon atoms), an alkoxy group (preferably having 1 to 4 carbon atoms, such as methoxy and ethoxy), an alkoxycarbonyl group (preferably having 1 to 4 carbon atoms), a trihalomethyl group (wherein the three halogen atoms are as defined in the foregoing and may be the same or different from one another, trifluoromethyl is preferred) or a hydroxy group.

These substituent groups in the aforementioned formula (I) can be applied to the substituent groups to be used in the other formulae (II) to (V)

In addition, in the general formula (I), $R^1$ can be substituted independently for all hydrogen atoms on the ring (including a case in which B and Z are $CR^1$) so that even if it is entirely unsubstituted with substituent groups other than a hydrogen atom, it can be substituted with the same or different substituent groups other than a hydrogen atom at one position or a plurality of positions. Such a general idea of substituent groups can be applied to $R^4$ and also to the substituent groups to be used in the other formulae (II) to (V).

The compound of the present invention represented by the formula (I) (hereinafter, referred to as compound (I), the compounds represented by other formulae are also expressed in the same manner) can be obtained by reacting a compound (a-1) with a compound (b).

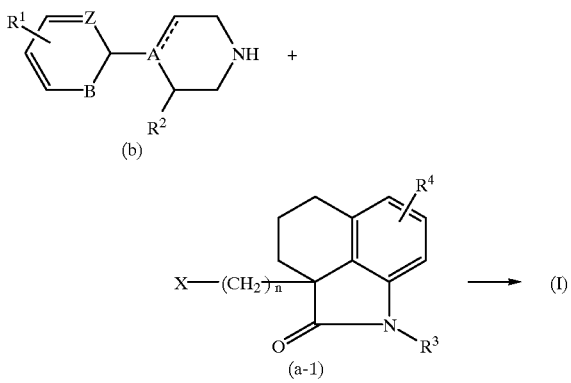

(In the above reaction formula, A, B, Z, $R^1$, $R^2$, $R^3$, $R^4$, X and n are as defined in the foregoing.)

The reaction for obtaining the compound (I) is carried out in the presence or absence of a base (however, a material substance is excluded as will be described later) without solvent or after dilution with an inert solvent and progresses at a temperature within the range of from ordinary temperature to heating temperature.

Examples of the inert solvent to be used include alcohols such as ethanol, ketones such as acetone or methyl ethyl ketone, dioxane, tetrahydrofuran, acetonitrile, dimethylformamide and the like, and examples of the base include salts of alkali metals such as sodium carbonate, potassium carbonate and the like carbonates and sodium bicarbonate, potassium bicarbonate and the like bicarbonates, trialkylamines, pyridine bases, and the like, as well as the compound (b) itself which is a secondary amine to be used as a material substance but can also be used as a base when used in an excess amount. In this connection, the base also exerts its functions as a reaction catalyst and an acid absorbent which neutralizes an acid formed as a result of the reaction.

The compound (II) can be obtained by allowing the compound (a-1) and a compound (b-1) to react with each other in accordance with the reaction conditions for the formation of compound (I).

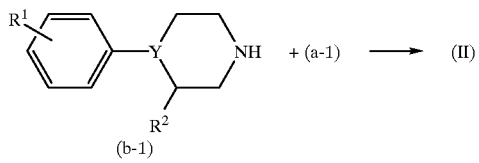

(In the above reaction formula, Y, $R^1$ and $R^2$ are as defined in the foregoing.)

The compound (III) can be obtained by allowing the compound (a-1) and a compound (b-2) to react with each other in accordance with the reaction conditions for the formation of compound (I).

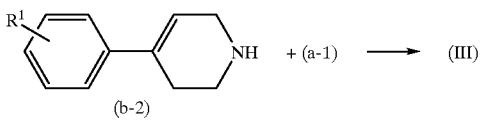

(In the above reaction formula, $R^1$ is as defined in the foregoing.)

The compound (IV) can be obtained by allowing the compound (a-1) and a compound (b-3) to react with each other in accordance with the reaction conditions for the formation of compound (I).

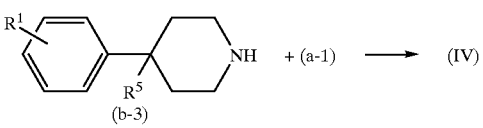

(In the above reaction formula, $R^1$ and $R^5$ are as defined in the foregoing.)

The compound (V) can be obtained by allowing the compound (a-1) and a compound (b-4) to react with each other in accordance with the reaction conditions for the formation of compound (I).

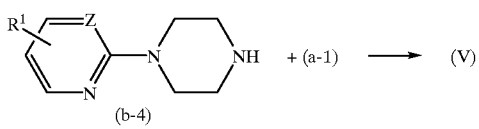

(In the above reaction formula, $R^1$, Z and n are as defined in the foregoing.)

The compound (b-1) as the material for the synthesis of the aforementioned compound (II) is a member of 1-phenylpiperazines when Y is N or a member of 4-phenylpiperidines when Y is CH. Also, the compound (b-2) as the material for the synthesis of the compound (III) is a member of 4-phenyl-1,2,3,6-tetrahydropyridines.

Illustrative typical examples of the 1-phenylpiperazines are shown in the following; 1-phenylpiperazine, 1-(2-fluorophenyl)piperazine, 1-(4-fluorophenyl)piperazine, 1-(2-chlorophenyl)piperazine, 1-(3-chlorophenyl) piperazine, 1-(4-chlorophenyl)piperazine, 1-(4-bromophenyl)piperazine, 1-(2-methoxyphenyl)piperazine, 1-(3-methoxyphenyl)piperazine, 1-(4-methoxyphenyl) piperazine, 1-(2-ethoxyphenyl)piperazine, 1-(2-isopropyloxyphenyl)piperazine, 1-(3-trifluoromethylphenyl)piperazine, 1-(2-methylphenyl)

piperazine, 1-(3-methylphenyl)piperazine, 1-(4-methylphenyl)piperazine, 1-(2,3-dimethylphenyl)piperazine, 1-(2,5-dimethylphenyl)piperazine, 1-(2,6-dimethylphenyl) piperazine, 1-(3,4-dimethylphenyl)piperazine, 1-(4-nitrophenyl)piperazine, 1-(4-acetylphenyl) piperazine, 1-(2-acetylphenyl)piperazine, 1-(3-methylphenyl)2-methylpiperazine, 1-(4-chlorophenyl)2-methylpiperazine, 1-(3-methoxyphenyl)2-methylpiperazine, 4-(4-sulfamoyl)-piperazine, 4-(4-carbamoylphenyl) piperazine and the like Illustrative typical examples of the 4-phenylpiperidines are shown in the following; 4-phenylpiperidine, 4-(4-fluorophenyl)piperidine, 4-(4-chlorophenyl)piperidine, 4-(4-bromophenyl)piperidine, 4-(3-trifluoromethylphenyl) piperidine, 4-(4-chloro-3-trifluoromethylphenyl)piperidine, 4-(2-methoxyphenyl)piperidine and the like.

Illustrative typical examples of the 4-phenyl-1,2,3,6-tetrahydropyridines are shown in the following; 4-phenyl-1,2,3,6-tetrahydropyridine, 4-(4-chlorophenyl)-1,2,3,6-tetrahydropyridine, 4-(4-fluorophenyl)-1,2,3,6-tetrahydropyridine, 4-(2-methoxyphenyl)-1,2,3,6-tetrahydropyridine, 4-(4-methylphenyl)-1,2,3,6-tetrahydropyridine and the like.

The compound (b-3) as the material for the synthesis of the aforementioned compound (IV) is a member of 4-phenylpiperidines in which the 4-position $R^5$ can have the aforementioned substituent groups other than hydrogen atom.

Illustrative examples of such 4-phenylpiperidines include 4-hydroxy-4-phenylpiperidine, 4-cyano-4-phenylpiperidine, 4-methoxy-4-phenylpiperidine, 4-methyl-4-phenylpiperidine, 4-acetyl-4-phenylpiperidine, 4-carboxy-4-phenylpiperidine, 4-methoxycarbonyl-4-phenylpiperidine, 4-(4-chlorophenyl)-4-hydroxypiperidine, 4-(4-bromophenyl)-4-hydroxypiperidine, 4-(3-trifluoromethylphenyl)-4-hydroxypiperidine and the like.

The compound (b-4) as the material for the synthesis of the aforementioned compound (V) is a member of piperazines having a nitrogen-containing heterocyclic ring on the 1-position.

Illustrative examples of such piperazines are shown below;
1-(2-pyridyl)piperazine,
1-(3-trifluoromethylpyridin-2-yl)piperazine,
1-(4-trifluoromethylpyridin-2-yl)piperazine,
1-(5-trifluoromethylpyridin-2-yl)piperazine,
1-(6-trifluoromethylpyridin-2-yl)piperazine, pyrimidin-2-yl-piperazine.

The compound of formula (a-1) as the other one of the materials to be used in the synthesis of the compound of the present invention represented by the formula (I) is produced from commercially available reagents in the following manner. That is, in the case of a compound (a-2) in which $R^3$ and $R^4$ in the formula (a-1) are both hydrogen atoms, 2a,3,4,5-tetrahydrobenz[cd]indole-2(1H)-one (a-2-0) is used as a first reagent,

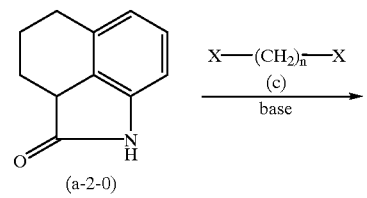

(a-2-0)

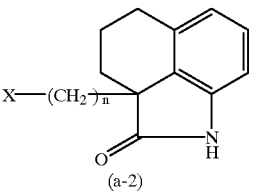

(a-2)

and the compound of interest is produced by allowing this reagent to react with a second reagent of the formula (c), X—(CH$_2$)$_n$—X (wherein X and n are as defined in the foregoing), in an inert solvent in the presence of a base. Preferably, dimethylformamide can be exemplified as the solvent, and sodium hydride as the base.

Examples of the compound (c) include those in which X is a halogen atom such as chlorine atom, bromine atom and iodine atom, and its more preferred examples include 1,3-dibromopropane, 1,4-dibromobutane, 1,5-dibromopentane and 1,6-dibromohexane. Other examples of the compound (c) include disulfonic acid esters, and 1,3-dimethanesulfonyloxypropane and the like alkylsulfonic acid diesters or 1,4-dibenzenesulfonyloxybutane and the like arylsulfonic acid diesters can be used.

The compound (c) belongs to a so-called reactive intermediate and can be obtained as a synthetic reagent or synthesized from diols represented by a formula HO—(CH$_2$)$_n$—OH (wherein n is an integer of 2 to 6). That is, it can be obtained as a dihalide by allowing diols to react with thionyl chloride or thionyl bromide or as a disulfonate by allowing diols to react with methanesulfonyl chloride or the like alkylsulfonic acid halide or benzenesulfonyl chloride or the like arylsulfonic acid halide. In addition, as another example of the halogenation, a halogenation reaction which is carried out using carbon tetrachloride or carbon tetrabromide in the presence of triphenylphosphine can also be used.

A compound (a-3) in which $R^4$ of the compound (a-1) is a hydrogen atom and $R^3$ is not a hydrogen atom can be obtained by using a compound (a-0), namely benz[cd]indole-2(1H)-one, as the starting material, allowing the material to react with a compound represented by the formula (d) [wherein X is a halogen atom, a methanesulfonyloxy, ethanesulfonyloxy or the like alkylsulfonic acid ester residue or a benzenesulfonyloxy, p-toluenesulfonyloxy or the like arylsulfonic acid ester residue, and $R^3$ is a lower alkyl or aralkyl group] in the presence of a base to obtain a compound (a-0-1), allowing the resulting compound to undergo its reaction using Raney nickel as a catalyst in an atmosphere of hydrogen to obtain a compound (a-3-0) and then allowing the thus obtained compound to react with the compound (c).

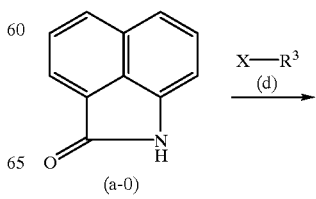

(a-0)

-continued

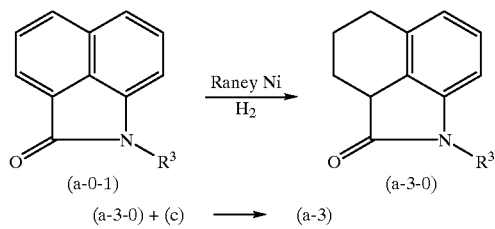

(a-3-0) + (c) ⟶ (a-3)

Examples of the compound (d) shown in the above reaction formula include those in which X is a halogen atom such as chlorine, bromine and iodine, and more preferred examples of the compound (d) include bromomethane, iodomethane, bromoethane, iodoethane, 1-bromo-2-methylpropane, 1-iodo-2-methylpropane, 1-bromopropane and 1-bromobutane. Other examples of the compound (d) include sulfonic acid esters, and methyl methanesulfonate and the like alkylsulfonic acid esters or 1-benzenesulfonyloxyethane and the like arylsulfonic acid esters can be used.

The compound (d) is generally obtained as a commercially available reagent or synthesized from alcohols represented by a formula HO—$R^3$ (wherein $R^3$ is as defined in the foregoing) in the same manner as the case of the compound (c).

As shown in the aforementioned reaction formula, the compound (a-0-1) is converted into the compound (a-3-0) through its catalytic hydrogenation in the presence of Raney nickel. This reaction is carried out after dilution with a polar solvent or a non-polar solvent and progresses under ordinary pressure or a pressurized condition. Examples of the solvent to be used include water, alcohol, acetic acid and the like polar solvents and ether, benzene, hexane and the like non-polar solvents.

A compound (a-4) in which $R^3$ of the compound (a-1) is a hydrogen atom and $R^4$ is not a hydrogen atom can be obtained by carrying out substitution reaction of at least one of the 6- to 8-positions of the aromatic ring of the compound (a-2-0), thereby firstly obtaining a compound (a-4-0), and then allowing the thus obtained compound to react with the compound (c), or by carrying out substitution reaction of at least one of the 6- to 8-positions of the aromatic ring of the compound (a-1-0) in which $R^3$ and $R^4$ of the compound (a-1) are hydrogen atoms.

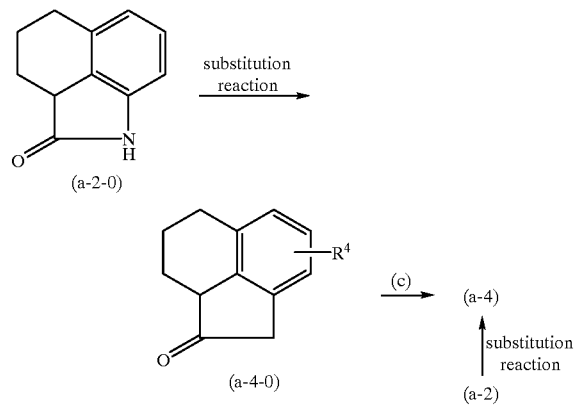

It is desirable to carry out introduction of a substituent group into the aromatic ring by a well known aromatic electrophilic substitution reaction. Examples of the aromatic electrophilic substitution reaction include halogenation, alkylation and acylation using the Friedel-Crafts reaction, nitration and the like.

In a preferred example of the halogenation, the reaction is carried out at a temperature of from 0° C. to reflux temperature in a solvent such as carbon disulfide, carbon tetrachloride, chloroform, dichloromethane, 1,2-dichloroethane and acetic acid in the presence or absence of an appropriate catalyst. Examples of the halogenation agent to be used include fluorine, chlorine, bromine and iodine, as well as unsubstituted or substituted N-fluoropyridinium salts such as 1-fluoropyridinium trifurate and 1-fluoro-2,6-dichloropyridinium tetrafluoroborate, N-fluoro-N-alkyl-sulfonamides such as N-fluoro-N-propyl-p-toluenesulfonamide, N-fluorosulfonimides such as N-fluorobenzenesulfonimide, sodium hypochlorite, N-bromosuccinimide, and the like.

The Friedel-Crafts reaction is carried out at a temperature of from 0° C. to reflux temperature in a solvent such as carbon disulfide, chloroform, dichloromethane, 1,2-dichloroethane and nitrobenzene in the presence of a catalyst. Examples of the alkylation agent to be used include halogenated hydrocarbons, as well as alcohols such as methanol and ethanol and olefin compounds such as propene. Examples of the acylation agent to be used include acyl halides such as acetyl chloride and propyl chloride, as well as acid anhydrides such as acetic anhydride, and carboxylic acids such as acetic acid and propionic acid. Alternatively, an acid chloride derivative is obtained using oxalic acid chloride, triphosgene or the like and then hydrolyzed using water, alcohol, amines and the like to convert it into respective carboxylic acid derivative, ester derivative and amide derivative. Examples of the catalyst to be used desirably include Lewis acids such as aluminum chloride, iron chloride, boron trifluoride, tin chloride and zinc chloride, as well as proton acids such as hydrogen fluoride, sulfuric acid and polyphosphoric acid.

In an example of the nitration, the reaction is carried out using concentrated nitric acid and concentrated sulfuric acid or using nitric acid in water, acetic acid or acetic anhydride solution. In addition, ethyl nitrate and the like nitric acid esters, acetyl nitrate and the like mixed acids and nitronium tetrafluoroborate and the like nitronium salts can also be used.

As occasion demands, the substituent group $R^4$ introduced into the aromatic ring may be converted into other substituent group by a chemical reaction. The reaction may be carried out either before the reaction with the compound (b) or after completion of the reaction with the compound (b).

For example, acetyl group or the like acyl group can be converted into corresponding acyloxy group by allowing it to react with peroxide such as m-chloroperbenzoic acid and pertrifluoroacetic acid in the presence of trifluoroacetic acid or the like acid catalyst as occasion demands, thereby effecting insertion of oxygen atom between the aromatic ring and carbonyl group. Thereafter, the acyloxy group can be converted into hydroxyl group by removing the acyl group through hydrolysis or the like method and then into an alkoxy group by the reaction of methyl iodide or the like alkylation agent in the presence of a base such as potassium carbonate and sodium bicarbonate. Also, methoxycarbonyl group or the like ester group can be converted into carbamoyl group, an amide derivative, a hydrazide derivative, a hydroxamic acid derivative or the like, when it is allowed to react, directly or after its hydrolysis into carboxylic acid, with ammonia, a primary amine, a secondary amine, hydrazine, hydroxylamine or the like via an active ester or the like reactive derivative.

Also, when the compound (I) in which $R^3$ and $R^4$ have substituent groups other than a hydrogen atom is synthesized, it is desirable that the compound (a-3) or (a-3-0) is firstly obtained, substitution of a hydrogen atom on the aromatic ring is carried out in the same manner as described in the foregoing and then the thus treated compound is allowed to react with the compound (b), directly in the former case or after converting it into the compound (a-1) by its reaction with the compound (c) in the latter case.

In addition, the compound (I) can also be synthesized by the following method.

The compound (I) can also be synthesized by the use of an alkene compound represented by a formula $CH_2=CH-(CH_2)_{n-1}-X$ [wherein n and X are as defined in the foregoing] or using a compound represented by formula: $W-(CH_2)_n-X$ [wherein W is a protected hydroxyl group (for example, benzyloxy group, acyloxy group and the like), and n and X are as defined in the foregoing], in stead of the compound (c). That is, as shown in the following reaction formula,

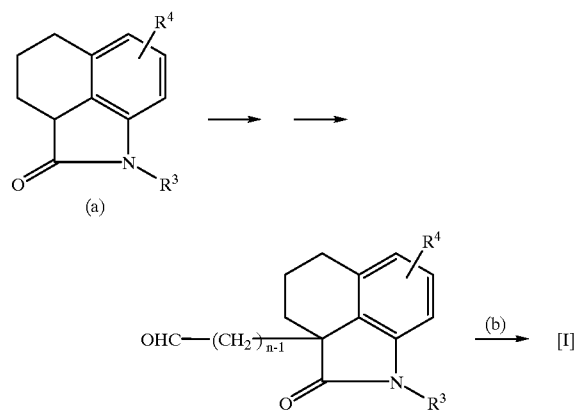

the compound (I) of interest can be obtained by allowing the compound (a) to react with these compounds in the presence of a base and then allowing osmium tetroxide and sodium periodate to react with the alkenes to effect conversion into an aldehyde compound, or, after de-protection of W, carrying out oxidation to effect conversion into an aldehyde compound and then carrying out reductive aminoalkylation reaction of the aldehyde compound with the compound (b) using sodium triacetoxyborate or the like reducing agent.

In the synthesis of the compound of the present invention, purification of a compound of interest from the reaction mixture is carried out by employing usually used techniques in the field of chemical synthesis, namely by effecting partition extraction of the reaction product into water and an organic solvent which does not optionally mixed with water, such as benzene, toluene, ethyl acetate, butyl acetate, methyl isobutyl ketone, chloroform, dichloromethane or the like solvent, and then carrying out concentration, crystallization and the like techniques. Also, as occasion demands, fractional purification may be carried out for example by a column chromatography using alumina or silica gel.

Being an amine, the compound (I) of the present invention exists as a base. In consequence, it forms salts with a number of inorganic and organic acids, and such a property is applied to its provisional forms as pharmaceutical preparations. That is, in its production process, acidification of the compound renders possible its solubilization and extraction purification in a polar solvent such as water so that it can be isolated as a salt having desirable physico-chemical properties, and, in applying it to pharmaceutical preparations, it can form a pharmacologically acceptable salt. Examples of the salt to be formed include acid addition salts with inorganic acids such as hydrochloric acid, nitric acid, hydrobromic acid and sulfuric acid or with aliphatic monocarboxylic acids, dicarboxylic acids, hydroxyalkanoic acids, hydroxyalkanoic diacids, amino acids and the like, as well as salts derived from aromatic acids, aliphatic and aromatic sulfonic acids and the like nontoxic organic acids. Examples of such acid addition salts include hydrochloride, hydrobromide, nitrate, sulfate, hydrogensulfate, phosphate, monohydrogenphosphate, dihydrogenphosphate, acetate, propionate, tartarate, oxalate, malonate, succinate, fumarate, maleate, mandelate, benzoate, phthalate, methanesulfonate, benzenesulfonate, toluenesulfonate, citrate, lactate, malate, glycolate and the like.

These acid addition salts described above are significant also as pharmacologically acceptable pharmaceutical compositions, and it seems that they have advantages as pharmaceutical compositions in terms of the preparation of medicaments and of the dispersing and absorbing abilities when administered to the human body.

A pharmaceutical composition which contains the compound of the present invention as an active ingredient can be administered to human and animals through the route of either oral administration or parenteral administration (for example, intravenous injection, intramuscular injection, subcutaneous injection, rectal administration, percutaneous absorption and the like). Thus, the pharmaceutical composition containing the compound of the present invention as an active ingredient can be made into appropriate dosage forms depending on each route of administration.

Illustrative examples of dosage forms include tablets, capsules, powders, granules, syrups and the like as oral preparations and intravenous, intramuscular and the like injections, rectal administration preparations, oleaginous suppositories, aqueous suppositories and the like as parenteral preparations.

Each of these various preparations can be produced in the usual way making use of generally used fillers, disintegrators, binders, lubricating agents, coloring agents and the like.

For example, lactose, glucose, corn starch, sorbitol, crystalline cellulose and the like can be exemplified as the fillers, starch, sodium alginate, gelatin powder, calcium carbonate, calcium citrate, dextrin and the like can be cited as the disintegrators, dimethyl cellulose, polyvinyl alcohol, polyvinyl ether, methyl cellulose, ethyl cellulose, acacia, gelatin, hydroxypropyl cellulose, polyvinyl pyrrolidone and the like can be exemplified as the binders, and talc, magnesium stearate, polyethylene glycol, hardened plant oil and the like can be exemplified as the lubricating agents. In addition, the aforementioned injections can be produced by further adding a buffer, a pH adjusting agent, a stabilizing agent and the like as occasion demands.

Though the amount of the compound of the present invention in the pharmaceutical composition varies depending on its dosage forms, it may be used in an amount of generally from 0.1 to 50% by weight, preferably from 0.1 to 20% by weight, based on the total composition. Its dose is optionally decided in each case, taking age, body weight, sex, difference in diseases, degree of symptoms and the like of each patient into consideration, but the dose is within the range of generally from 1 to 1,000 mg, preferably from 1 to 300 mg, per day per adult, and the daily dose is administered once a day or by dividing it into several doses per day.

The pharmaceutical composition of the present invention can be used for the treatment or prevention of manic-depressive psychosis, anxiety, schizophrenia, gastrointestinal disease, jet lag and the like.

BEST MODE OF CARRYING OUT THE INVENTION

Inventive and test examples of the present invention are given below by way of illustration and not by way of limitation.

EXAMPLE 1

2a-(4-Bromobutyl)-2a,3,4,5-tetrahydrobenz[cd]indole-2(1H)-one 2a, 3,4,5-Tetrahydrobenz [cd]indole-2(1H) -one (3.0 g, 17 mmol) was dissolved in anhydrous N,N-dimethylformamide (120 ml). Thereto was added an oily sodium hydride (760 mg, 19 mmol), and the resulting solution was stirred at a room temperature for 1 hour. The reaction solution was mixed with 1,4-dibromobutane (6.3 ml, 52 mmol) and again stirred for 17 hours. The solvent was evaporated under a reduced pressure, and the thus obtained residue was mixed with ethyl acetate, water and hydrochloric acid (1 N). The reaction product was extracted with ethyl acetate, washed with saturated brine and dried with anhydrous sodium sulfate. Then the compound obtained by the evaporation of the solvent under a reduced pressure was separated and purified by a silica gel column chromatography to obtain 1.8 g of the title compound (5.8 mmol, 33% in yield).

$^1$H-NMR (CDCl$_3$) δ 1.17–1.28 (1 H, m), 1.32–1.51 (2 H, m), 1.72–1.90 (5 H, m), 2.06–2.19 (2 H, m), 2.60–2.70 (1 H, m), 2.80–2.89 (1 H, m), 3.30 (2 H, t, J=7.0 Hz), 6.67 (1 H, d, J=7.4 Hz), 6.81 (1 H, d, J=7.8 Hz), 7.12 (1 H, dd), 7.34 (1 H, br s); MW 308.22 (C$_{15}$H$_{18}$BrNO); Mass spectrum ESI m/z 307:309=1:1 (M)$^+$

EXAMPLE 2

2a-(3-Bromopropyl)-2a, 3,4,5-tetrahydrobenz[cd]indole-2(1H)-one 2a, 3,4,5-Tetrahydrobenz [cd]indole-2(1H) -one (1.0 g, 5.8 mmol) was dissolved in anhydrous N,N-dimethylformamide (40 ml). Thereto was added sodium hydride (230 mg, 5.8 mmol), and the resulting solution was stirred at 60° C. for 1 hour. The reaction solution was mixed with 1,3-dibromopropane (1.8 ml, 17 mmol) and again stirred for 2 hours. The solvent was evaporated under a reduced pressure, and the thus obtained residue was mixed with ethyl acetate and water. The reaction product was extracted with ethyl acetate, washed with saturated brine and dried with anhydrous sodium sulfate. Then the compound obtained by the evaporation of the solvent under a reduced pressure was separated and purified by a silica gel column chromatography to obtain 150 mg of the title compound (0.51 mmol, 8.8% in yield).

$^1$H-NMR (CDCl$_3$) δ 1.32–1.44 (1 H, m), 1.62–1.73 (1 H, m), 1.81–2.03 (1 H, m), 2.08–2.22 (2 H, m), 2.62–2.71 (1 H, m), 2.83–2.92 (1 H, m), 3.24–3.34 (2 H, m), 6.69 (1 H, d, J=7.6 Hz), 6.82 (1 H, d, J=8.0 Hz), 7.13 (1 H, dd), 7.70 (1 H, br s); MW 294.19 (C$_{14}$H$_{16}$BrNO); Mass spectrum EIMS m/z 293:295=1:1 (M)$^+$

EXAMPLE 3

2a-(5-Bromopentyl)-2a, 3,4,5-tetrahydrobenz[cd]indole-2(1H)-one 2a, 3,4,5-Tetrahydrobenz [cd]indole-2(1H) -one (1.0 g, 5.8 mmol) was dissolved in anhydrous N,N-dimethylformamide (40 ml). Thereto was added sodium hydride (250 mg, 6.3 mmol), and the resulting solution was stirred at a room temperature for 1 hour. The reaction solution was mixed with 1,5-dibromopentane (2.4 ml, 17 mmol) and again stirred for 17 hours. The solvent was evaporated under a reduced pressure, and the thus obtained residue was mixed with ethyl acetate and water. The reaction product was extracted with ethyl acetate, washed with saturated brine and dried with anhydrous sodium sulfate. Then the compound obtained by the evaporation of the solvent under a reduced pressure was separated and purified by a silica gel column chromatography to obtain 230 mg of the title compound (0.70 mmol, 12% in yield).

$^1$H-NMR (CDCl$_3$) δ 1.03–1.15 (1 H, m), 1.25–1.44 (4 H, m), 1.71–1.92 (5 H, m), 2.02–2.19 (2 H, m), 2.60–2.70 (1 H, m), 2.77–2.90 (1 H, m), 3.32 (2 H, t, J=7.0 Hz), 6.67 (1 H, d, J=7.4 Hz), 6.81 (1 H, d, J=7.4 Hz), 7.12 (1 H, dd), 7.30 (1 H, br s); MW 322.24 (C$_{16}$H$_{20}$BrNO); Mass spectrum EIMS m/z 321:323=1:1 (M)$^+$

EXAMPLE 4

4-Phenylpiperidine hydrochloride 1,2,3,6-Tetrahydro-4-phenylpyridine hydrochloride (200 mg, 1.0 mmol) and 10% palladium-carbon (30 mg) were stirred in methanol (2 ml) for 19 hours in an atmosphere of hydrogen. The reaction solution was filtered and the resulting residue was thoroughly washed with methanol. Then the filtrate and washed solution were combined and evaporated under a reduced pressure to obtain 190 mg of the title compound (0.95 mmol, 93% in yield).

$^1$H-NMR (CDCl$_3$) δ 2.01–2.10 (2 H, m), 2.17–2.30 (2 H, m), 2.72–2.82 (1 H, m), 2.98–3.07 (2 H, m), 3.60–3.68 (2 H, m), 7.22–7.29 (3H, m), 7.31–7.37 (2 H, m); MW 197.71 (C$_{11}$H$_{16}$ClN); Mass spectrum EIMS m/z 161 (M)$^+$

EXAMPLE 5

2a-[4-{4-(2-Methoxyphenyl)piperazinyl}butyl]-2a,3,4,5-tetrahydrobenz[cd]indole-2(1H)-one 2a-(4-Bromobutyl)-2a,3,4,5-tetrahydrobenz[cd]indole-2(1H)-one (220 mg, 0.72 mmol), 4-(2-methoxyphenyl)piperazine (150 mg, 0.79 mmol) and potassium carbonate (150 mg, 1.1 mmol) were stirred in anhydrous N,N-dimethylformamide (5 ml) at 50° C. for 4 hours. The solvent was evaporated under a reduced pressure, and the thus obtained residue was mixed with ethyl acetate and water. The reaction product was extracted with ethyl acetate, washed with saturated brine and dried with anhydrous sodium sulfate. Then the compound obtained by the evaporation of the solvent under a reduced pressure was separated and purified by a silica gel column chromatography to obtain 280 mg of the title compound (0.68 mmol, 94% in yield).

$^1$H-NMR (CDCl$_3$) δ 1.04–1.15 (4 H, m), 1.26–1.51 (4 H, m), 1.76–1.92 (3 H, m), 2.07–2.20 (2 H, m), 2.25–2.38 (2 H, m), 2.54–2.68 (5 H, m), 2.80–2.90 (1 H, m), 3.05 (4 H, br s), 3.85 (3 H, s), 6.84 (1 H, d, J=8.2 Hz), 6.88–7.00 (3 H, m), 7.12 (1 H, dd, J=7.6, 7.6 Hz), 7.42 (1 H, br s); MW 419.57 (C$_{26}$H$_{33}$N$_3$O$_2$); Mass spectrum ESI m/z 420 (M+H)$^+$ The thus obtained free compound was dissolved in hydrochloric acid-saturated methanol to obtain its hydrochloric acid salt.

MW 456.03 (C$_{26}$H$_{34}$ClN$_3$O$_2$); Mass spectrum EIMS m/z 419 (M−HCl)$^+$

EXAMPLE 6

2a-[4-(4-Phenyl-1,2,3,6-tetrahydropyridyl)butyl]-2a,3,4,5-tetrahydrobenz[cd]indole-2(1H)-one This compound was synthesized in the same manner as described in Example 5, except that 1,2,3,6-tetrahydro-4- phenylpyridine hydrochloride was used in stead of 4-(2-methoxyphenyl)piperazine (yield, 56%).

$^1$H-NMR (CDCl$_3$) δ 1.04–1.16 (1 H, m), 1.25–1.55 (4 H, m), 1.77–1.93 (3 H, m), 2.07–2.20 (2 H, m), 2.29–2.42 (2 H, m), 2.50–2.57 (2 H, m), 2.60–2.69 (3 H, m), 2.80–2.89 (1 H, m), 3.10 (2 H dd, J=6.3, 2.7 Hz), 6.02 (1 H, s), 6.67 (1 H, d, J=7.8 Hz), 6.80 (1 H, d, J=7.8 Hz), 7.11 (1 H, dd), 7.19–7.38 (5 H, m), 7.54 (1 H, br s); MW 386.54 (C$_{26}$H$_{30}$N$_2$O); Mass spectrum EIMS m/z 386 (M)$^+$ The thus obtained free compound was dissolved in hydrochloric acid-saturated methanol to obtain its hydrochloric acid salt.

MW 423.00 (C$_{26}$H$_{31}$ClN$_2$O); Mass spectrum EIMS m/z 386 (M–HCl)

EXAMPLE 7

2a-[4-{4-(2-Ethoxyphenyl)piperazinyl}butyl]-2a,3,4,5-tetrahydrobenz[cd]indole-2(1H)-one This compound was synthesized in the same manner as described in Example 5, except that 4-(2-ethoxyphenyl)piperazine hydrochloride was used in stead of 4-(2-methoxyphenyl)piperazine.

$^1$H-NMR (CDCl$_3$) δ 1.04–1.14 (1 H, m), 1.32–1.39 (1 H, m), 1.44 (3 H, t, J=7.1 Hz), 1.75–1.92 (3 H, m), 2.08–2.19 (2 H, m), 2.25–2.38 (2 H, m), 2.53–2.69 (5 H, m), 2.80–2.90 (1 H, m), 3.02–3.14 (4 H, br s), 4.05 (2 H, q), 6.67 (1 H, d, J=7.6 Hz), 6.79–6.98 (5 H, m), 7.11 (1 H, dd, J=8.0 Hz), 7.39 (1 H, br s); MW 433.59 (C$_{27}$H$_{36}$ClN$_3$O$_2$); Mass spectrum TS m/z 434 (M+H)$^+$ The thus obtained free compound was dissolved in hydrochloric acid-saturated methanol to obtain its hydrochloric acid salt.

MW 470.05 (C$_{27}$H$_{36}$ClN$_3$O$_2$); Mass spectrum EIMS m/z 433 (M–HCl)$^+$

EXAMPLE 8

2a-[4-(4-Phenylpiperazinyl)butyl]-2a,3,4,5-tetrahydrobenz[cd]indole-2(1H)-one

This compound was synthesized in the same manner as described in Example 5, except that 4-phenylpiperazine hydrochloride was used in stead of 4-(2-methoxyphenyl)piperazine (yield, 91%).

$^1$H-NMR (CDCl$_3$) δ 5 1.03–1.15 (1 H, m), 1.25–1.51 (4 H, m), 1.75–1.92 (3 H, m), 2.07–2.20 (2 H, m), 2.24–2.36 (2 H, m), 2.49–2.56 (4 H, m), 2.60–2.69 (1 H, m), 2.80–2.88 (1 H, m), 3.13–3.19 (4 H, m), 6.67 (1 H, d, J=7.6 Hz), 6.79–6.86 (2 H, m), 6.91 (2 H, d, J=8.4 Hz), 7.11 (1 H, dd), 7.22–7.29 (2 H, m), 7.50 (1 H, br s); MW 389.54 (C$_{25}$H$_{31}$N$_3$O); Mass spectrum EIMS m/z 389 (M)$^+$ The thus obtained free compound was dissolved in hydrochloric acid-saturated methanol to obtain its hydrochloric acid salt.

MW 426.00 (C$_{25}$H$_{32}$ClN$_3$O); Mass spectrum LC m/z 390 (M+H)$^+$

EXAMPLE 9

2a-[4-(4-Phenylpiperidyl)butyl]-2a,3,4,5-tetrahydrobenz[cd]indole-2(1H)-one

This compound was synthesized in the same manner as described in Example 5, except that 4-phenylpiperidine hydrochloride (Example 4) was used in stead of 4-(2-methoxyphenyl)piperazine (yield, 91%).

$^1$H-NMR (CDCl$_3$) δ 1.02–1.14 (1 H, m), 1.22–1.54 (4 H, m), 1.75–1.93 (7 H, m), 2.07–2.20 (2 H, m), 2.23–2.36 (2 H, m), 2.41–2.51 (1 H, m), 2.60–2.70 (1 H, m), 2.80–2.90 (1 H, m), 2.95–3.04 (2 H, m), 6.67 (1 H, d, J=7.8 Hz), 6.81 (1 H, d, J=7.8 Hz), 7.12 (1 H, dd), 7.26–7.24 (3 H, m), 7.25–7.33 (3 H, m); MW 388.55 (C$_{26}$H$_{32}$N$_2$O); Mass spectrum LC m/z 389 (M+H)$^+$ The thus obtained free compound was dissolved in hydrochloric acid-saturated methanol to obtain its hydrochloric acid salt.

MW 425.01 (C$_{26}$H$_{33}$ClN$_2$O); Mass spectrum LC m/z 389 (M–HCl+H)$^+$

EXAMPLE 10

2a-[4-{4-(4-Methoxyphenyl)piperazinyl}-butyl]-2a,3,4,5-tetrahydrobenz[cd]indole-2(1H)-one This compound was synthesized in the same manner as described in Example 5, except that 4-(4-methoxyphenyl)piperazine hydrochloride was used in stead of 4-(2-methoxyphenyl)piperazine (yield, 61%).

$^1$H-NMR (CDCl$_3$) δ 1.03–1.14 (1 H, m), 1.25–1.52 (4 H, m), 1.75–1.91 (3 H, m), 2.05–2.20 (2 H, m), 2.23–2.35 (2 H, m), 2.50–2.57 (4 H, m), 2.60–2.70 (1 H, m), 2.80–2.90 (1 H, m), 3.01–3.09 (4 H, m), 3.76 (3 H, s), 6.66 (1 H, d, J=7.8 Hz), 6.79–6.89 (5 H, m), 7.11 (1 H, dd, J=7.4 Hz), 7.29 (1 H, br s); MW 419.57 (C$_{26}$H$_{33}$N$_3$O$_2$); Mass spectrum EIMS m/z 419 (M)$^+$ The thus obtained free compound was dissolved in hydrochloric acid-saturated methanol to obtain its hydrochloric acid salt.

MW 456.03 (C$_{26}$H$_{34}$ClN$_3$O$_2$); Mass spectrum EIMS m/z 419 (M–HCl)+

EXAMPLE 11

2a-[4-{4-(2-Methylphenyl)piperazinyl}butyl]-2a,3,4,5-tetrahydrobenz[cd]indole-2(1H)-one This compound was synthesized in the same manner as described in Example 5, except that 4- (2-methylphenyl)piperazine hydrochloride was used in stead of 4-(2-methoxyphenyl)piperazine (yield, 91%).

$^1$H-NMR (CDCl$_3$) δ 1.04–1.14 (1 H, m), 1.28–1.51 (4 H, m), 1.76–1.93 (3 H, m), 2.06–2.19 (2 H, m), 2.25–2.38 (5 H, m), 2.44–2.70 (5 H, m), 2.80–2.93 (5 H, m), 6.67 (1 H, d, J=7.8 Hz), 6.81 (1 H, d, J=7.4 Hz), 6.95–7.01 (3 H, m), 7.10–7.17 (2 H, m), 7.28 (1 H, br s); MW 403.57 (C$_{26}$H$_{33}$N$_3$O); Mass spectrum ElMS m/z 403 (M)$^+$ The thus obtained free compound was dissolved in hydrochloric acid-saturated methanol to obtain its hydrochloric acid salt.

MW 440.03 (C$_{26}$H$_{34}$ClN$_3$O); Mass spectrum EIMS m/z 403 (M–HCl)$^+$

EXAMPLE 12

2a-[4-{4-(3-Methoxyphenyl)piperazinyl}butyl]-2a,3,4,5-tetrahydrobenz[cd]indole-2(1H)-one This compound was synthesized in the same manner as described in Example 5, except that 4-(3-methoxyphenyl)piperazine hydrochloride was used in stead of 4-(2-methoxyphenyl)piperazine (yield, 85%).

$^1$H-NMR (CDCl$_3$) δ 1.03–1.15 (1 H, m), 1.24–1.50 (4 H, m), 1.75–1.92 (3 H, m), 2.05–2.20 (2 H, m), 2.22–2.35 (2 H, m), 2.47–2.55 (4 H, m), 2.60–2.69 (1 H, m), 2.79–2.89 (1 H, m), 3.12–3.18 (4 H, m), 6.40 (1 H, dd, J=8.2, 2.3 Hz), 6.44 (1 H, dd, J=2.3 Hz), 6.52 (1 H, dd, J=8.4 Hz), 6.66 (1 H, d, J=7.6 Hz), 6.81 (1 H, d, J=7.6 Hz), 7.09–7.17 (2 H, m), 7.31 (1 H, br s); MW 419.57 ($C_{26}H_{33}N_3O_2$); Mass spectrum EIMS m/z 419 (M)$^+$ The thus obtained free compound was dissolved in hydrochloric acid-saturated methanol to obtain its hydrochloric acid salt.

MW 456.03 ($C_{26}H_{34}ClN_3O_2$); Mass spectrum EIMS m/z 419 (M–HCl)$^+$

EXAMPLE 13

2a-[4-{4-(3-Trifluoromethylphenyl) piperazinyl}butyl]-2a,3,4,5-tetrahydrobenz[cd] indole-2(1H)-one This compound was synthesized in the same manner as described in Example 5, except that 4-(3-trifluoromethylphenyl)piperazine was used in stead of 4-(2-methoxyphenyl)piperazine (yield, 79%).

$^1$H-NMR (CDCl$_3$) δ 1.04–1.17 (1 H, m), 1.28–1.52 (4 H, m), 1.75–1.93 (3 H, m), 2.06–2.20 (2 H, m), 2.25–2.36 (2 H, m), 2.49–2.55 (4 H, m), 2.60–2.70 (1 H, m), 2.80–2.87 (1 H, m), 3.16–3.22 (4 H, m), 6.67 (1 H, d, J=7.6 Hz), 6.80 (1 H, d, J=8.0 Hz), 7.00–7.14 (1 H, m), 7.27–7.36 (2 H, m) MW 457.54 ($C_{26}H_{30}F_3N_3O$); Mass spectrum EIMS m/z 457 (M)$^+$ The thus obtained free compound was dissolved in hydrochloric acid-saturated methanol to obtain its hydrochloric acid salt.

MW 494.00 ($C_{26}H_{31}ClF_3N_3O$); Mass spectrum EIMS m/z 457 (M–HCl)$^+$

EXAMPLE 14

2a-[4-{4-(2-Chlorophenyl)piperazinyl}butyl]-2a,3,4, 5-tetrahydrobenz[cd]indole-2(1H)-one This compound was synthesized in the same manner as described in Example 5, except that 4-(2-chlorophenyl) piperazine hydrochloride was used in stead of 4-(2-methoxyphenyl)piperazine (yield, 95%).

$^1$H-NMR (CDCl$_3$) δ 1.03–1.16 (1 H, m), 1.29–1.51 (4 H, m), 1.76–1.92 (3 H, m), 2.06–2.20 (2 H, m), 2.26–2.39 (2 H, m), 2.51–2.69 (5 H, m), 2.80–2.90 (1 H, m), 3.00–3.08 (4 H, m), 6.67 (1 H, d, J=8.0 Hz), 6.81 (1 H, d, J=7.6 Hz), 6.95 (1 H, ddd, J=8.0, 7.2, 1.5 Hz), 7.03 (1 H, dd, J=8.0 Hz), 7.12 (1 H, dd), 7.20 (1 H, br s), 7.34 (1 H, dd); MW 423.98 ($C_{25}H_{30}ClN_3O$); Mass spectrum EIMS m/z 423:425=3:1 (M)$^+$ The thus obtained free compound was dissolved in hydrochloric acid-saturated methanol to obtain its hydrochloric acid salt.

MW 460.45 ($C_{25}H_{31}Cl_2N_3O$); Mass spectrum EIMS m/z 423:425=3:1 (M–HCl)$^+$

EXAMPLE 15

2a-[4-{4-(3-Methylphenyl)-3-methyl-piperazinyl}butyl]-2a,3,4,5-tetrahydrobenz[cd] indole-2(1H)-one This compound was synthesized in the same manner as described in Example 5, except that 2-methyl-1-(3-methylphenyl)piperazine was used in stead of 4-(2-methoxyphenyl)piperazine (yield, 90%).

$^1$H-NMR (CDC13) δ 0.99 (3 H, dd, J=6.4, 4.9 Hz), 1.05–1.18 (1 H, m), 1.30–1.50 (5 H, m), 1.75–1.92 (3 H, m), 2.07–2.40 (9 H, m), 2.45–2.51 (1 H, m), 2.60–2.70 (2 H, m), 2.80–2.90 (1 H, m), 3.01–3.19 (2 H, m), 6.64–6.75 (4 H, m), 6.80 (1 H, d, J=7.4 Hz), 7.09–7.15 (2 H, m), 7.21 (1 H, br s); MW 417.59 ($C_{27}H_{35}N_3O$); Mass spectrum EIMS m/z 417 (M)$^+$ The thus obtained free compound was dissolved in hydrochloric acid-saturated methanol to obtain its hydrochloric acid salt.

MW 454.05 ($C_{27}H_{36}ClN_3O$); Mass spectrum PB m/z 418 (M–HCl+H)$^+$

EXAMPLE 16

2a-[3-{4-(2-Methoxyphenyl)piperazinyl}propyl]-2a, 3,4,5-tetrahydrobenz[cd]indole-2(1H)-one This compound was synthesized in the same manner as described in Example 5, except that 2a-(3-bromopropyl)-2a, 3,4,5-tetrahydrobenz[cd]indole-2(1H)one (Example 2) was used in stead of 2a-(4-bromobutyl)-2a,3,4,5-tetrahydrobenz [cd]indole-2(1H)one (Example 1) (yield, 98%).

$^1$H-NMR (CDCl$_3$) δ 1.24–1.43 (3 H, m), 1.79–1.89 (3 H, m), 2.07–2.37 (4 H, m), 2.07–2.37 (4 H, m), 2.47–2.69 (5 H, m), 2.81–2.89 (1 H, m), 2.98–3.11 (4 H, m), 3.84 (3 H, s), 6.66 (1 H, d, J=7.6 Hz), 6.80 (1 H, d, J=8.0 Hz), 6.84 (1 H, d, J=8.4 Hz), 6.89–7.01 (3 H, m), 7.11 (1 H, dd), 7.22 (1 H, br s); MW 405.54 ($C_{25}H_{31}N_3O_2$); Mass spectrum TS m/z 406 (M+H)$^+$ The thus obtained free compound was dissolved in hydrochloric acid-saturated methanol to obtain its hydrochloric acid salt.

MW 442.00 ($C_{25}H_{32}ClClN_3O_2$); Mass spectrum ELIMS m/z 405 (M–HCl)$^+$

EXAMPLE 17

2a-[3-(4-Phenyl-1,2,3,6-tetrahydropyridyl)propyl]-2a,3,4,5-tetrahydrobenz[cd]indole-2(1H)-one This compound was synthesized in the same manner as described in Example 16, except that 1,2,3,6-tetrahydro-4-phenylpyridine hydrochloride was used in stead of 4-(2-methoxyphenyl)piperazine (yield, 72%).

$^1$H-NMR (CDCl$_3$) δ 1.25–1.42 (2 H, m), 1.53–1.69 (1 H, m), 1.78–1.94 (3 H, m), 2.08–2.21 (2 H, m), 2.29–2.42 (2 H, m), 2.48–2.56 (2 H, m), 2.56–2.69 (3 H, m), 2.81–2.89 (1 H, s), 3.04 (2 H, dd, J=6.1, 2.7 Hz), 6.00 (1 H, br s), 6.66 (1 H, d, J=7.4 Hz), 6.79 (1 H, d, J=7.8 Hz), 7.10 (1 H, dd), 7.19–7.37 (5 H, m), 7.52 (1 H, br s); MW 372.51 ($C_{25}H_{28}N_2O$); Mass spectrum EIMS m/z 372 (M)$^+$ The thus obtained free compound was dissolved in hydrochloric acid-saturated methanol to obtain its hydrochloric acid salt.

MW 408.97 ($C_{25}H_{29}ClN_2O$); Mass spectrum EIMS m/z 372 (M)$^+$

EXAMPLE 18

2a-[5-{4-(2-Methoxyphenyl)piperazinyl}pentyl]-2a, 3,4,5-tetrahydrobenz[cd]indole-2(1H)-one This compound was synthesized in the same manner as described in Example 5, except that 2a-(5-bromopentyl)-2a, 3,4,5-tetrahydrobenz[cd]indole-2(1H)one (Example 3) was used in stead of 2a-(4-bromobutyl)-2a,3,4,5-tetrahydrobenz [cd]indole-2(1H)one (Example 1) (yield, 91%).

$^1$H-NMR (CDCl$_3$) δ 1.04–1.15 (1 H, m), 1.17–1.50 (6 H, m), 1.73–1.90 (3 H, m), 2.06–2.19 (2 H, m), 2.28–2.35 (2 H.

m), 2.53–2.69 (5 H, m), 2.80–2.90 (1 H, m), 3.01–3.13 (4 H, m), 6.66 (1 H, d, J=7.6 Hz), 6.79–7.00 (5 H, m), 7.11 (1 H, dd, J=7.6 Hz), 7.21 (1 H, br s); MW 433.59 ($C_{27}H_{35}N_3O_2$); Mass spectrum FBB m/z 434 (M+H)$^+$ The thus obtained free compound was dissolved in hydrochloric acid-saturated methanol to obtain its hydrochloric acid salt.

MW 470.05 ($C_{27}H_{36}ClN_3O_2$); Mass spectrum EIMS m/z 433 (M–HCl)$^+$

EXAMPLE 19

2a-[5-(4-Phenyl-1,2,3,6-tetrahydropyridyl)pentyl]-2a,3,4,5-tetrahydrobenz[cd]indole-2(1H)-one This compound was synthesized in the same manner as described in Example 18, except that 1,2,3,6-tetrahydro-4-phenylpyridine hydrochloride was used in stead of 4-(2-methoxyphenyl)piperazine (yield, 81%).

$^1$H-NMR (CDCl$_3$) δ 1.04–1.14 (1 H, mn), 1.18–1.41 (5 H, m), 1.73–1.90 (3 H, m), 2.04–2.19 (2 H, m), 2.32–2.40 (2 H, m), 2.51–2.70 (5 H, m), 2.80–2.90 (1 H, m), 3.07–3.13 (2 H, m), 6.03 (1 H, s), 6.66 (1 H, d, J=7.6 Hz), 6.80 (1 H, d, J=8.0 Hz), 7.11 (1 H, dd), 7.19–7.40 (6 H, m)); MW 400.56 ($C_{27}H_{32}N_2O$); Mass spectrum EIMS m/z 400 (M)$^+$ The thus obtained free compound was dissolved in hydrochloric acid-saturated methanol to obtain its hydrochloric acid salt.

MW 437.02 ($C_{27}H_{33}ClN_2O$); Mass spectrum ElMS m/z 400 (M–HCl)$^+$

EXAMPLE 20

2a-[4-{4-(2,6-Dimethylphenyl)piperazinyl}butyl]-2a,3,4,5-tetrahydrobenz[cd]indole-2(1H)-one This compound was synthesized in the same manner as described in Example 5, except that 4-(2,6-dimethylphenyl)piperazine was used in stead of 4-(2-methoxyphenyl)piperazine (yield, 86%).

$^1$H-NMR (CDCl$_3$) δ 1.03–1.17 (1 H, m), 1.26–1.53 (4 H, m), 1.77–1.92 (3 H, m), 2.08–2.20 (2 H, m), 2.21–2.38 (8 H, m), 2.42–2.50 (4 H, m), 2.60–2.70 (1 H, m), 2.80–2.90 (1 H, m), 3.03–3.11 (4 H, m), 6.67 (1 H, d, J=7.8 Hz), 6.81 (1 H, d, J=7.8 Hz), 6.90–7.00 (3 H, m), 7.12 (1 H, dd), 7.40 (1 H, br s); MW 417.59 ($C_{27}H_{35}N_3O$); Mass spectrum ESP m/z 418 (M+H)$^+$ The thus obtained free compound was dissolved in hydrochloric acid-saturated methanol to obtain its hydrochloric acid salt.

MW 454.02 ($C_{27}H_{36}ClN_{3O}$); Mass spectrum ESP m/z 418 (M–HCl+H)$^+$

EXAMPLE 21

1-t-Butoxycarbonyl-4-hydroxy-4-(2-methoxyphenyl) piperidine

2-Bromoanisole (5.0 g, 27 mmol) was dissolved in anhydrous tetrahydrofuran (60 ml) to which, while stirring, was subsequently added dropwise n-butyl lithium hexane solution (17 ml, 27 mmol) spending 20 minutes at –78° C. in an atmosphere of argon. After additional 30 minutes of stirring, to this was added dropwise anhydrous tetrahydrofuran solution (40 ml) of 1-t-butoxycarbonyl-4-piperidone (5.3 g, 27 mmol) spending 40 minutes. After additional 3.5 hours of stirring, to this was added saturated ammonium chloride aqueous solution (200 ml). The reaction product was extracted with ethyl acetate, washed with saturated brine and dried with anhydrous sodium sulfate. Then 5.2 g of the aforementioned compound of interest (17 mmol, 63% in yield) was obtained by evaporating the solvent under a reduced pressure.

$^1$H-NMR (CDCl$_3$) δ 1.50 (9 H, s), 1.90–2.06 (4 H, m), 3.24–3.37 (2 H, m), 3.87–4.08 (5 H, m), 6.93–7.00 (2 H, m), 7.22–7.29 (2 H, m); MW 307.39 ($C_{17}H_{25}BrNO_4$); Mass spectrum EIMS m/z 307 (M)$^+$

EXAMPLE 22

1-t-Butoxycarbonyl-4-(2-methoxyphenyl)-1,2,3,6-tetrahydropyridine 1-t-Butoxycarbonyl-4-hydroxy-4-(2-methoxyphenyl) piperidine (230 mg, 0.75 mmol) was dissolved in methylene chloride (10 ml). Thereto was added trifluoroacetic acid (0.20 ml, 2.6 mmol) and the resulting solution was stirred at a room temperature for 2.5 hours. The reaction solution was washed with saturated sodium bicarbonate aqueous solution and saturated brine in that order and dried with anhydrous sodium sulfate. Then the compound obtained by the evaporation of the solvent under a reduced pressure was separated and purified by a silica gel column chromatography to obtain 150 mg of the aforementioned compound of interest (0.53 mmol, 71% in yield).

$^1$H-NMR (CDCl$_3$) δ 1.49 (9 H, s), 2.46–2.53 (2 H, m), 3.56–3.62 (2 H, m), 3.81 (3 H, s), 4.02–4.07 (2 H, m), 6.80–6.94 (2 H, m), 7.14 (1 H, dd, J=1.6, 7.4 Hz), 7.24 (1 H, ddd, J=7.4 Hz); MW 289.38 ($C_{17}H_{23}NO_3$); Mass spectrum EIMS m/z 289 (M)$^+$

EXAMPLE 23

1-t-Butoxycarbonyl-4-(2-methoxyphenyl)piperidine 1-t-Butoxycarbonyl-4-(2-methoxyphenyl)-1,2,3,6-tetrahydropyridine (150 mg, 0.52 mmol) and 10% palladium-carbon (30 mg) were stirred in methanol for two nights in an atmosphere of hydrogen. The reaction solution was filtered and the thus obtained residue was thoroughly washed with methanol. Then the filtrate and washed solution were combined and evaporated under a reduced pressure to obtain 120 mg of the aforementioned compound of interest (0.42 mmol, 81% in yield).

$^1$H-NMR (CDCl$_3$) δ 1.48 (9 H, s), 1.56–1.65 (2 H, m), 1.75–1.83 (2 H, m), 2.76–2.90 (2 H, m), 3.05–3.14 (1 H, m), 3.83 (3 H, s), 4.14–4.30 (2 H, m), 6.87 (1 H, d, J=8.2 Hz), 6.93 (1 H, dd, J=6.8, 7.7 Hz), 7.13–7.21 (2 H, m); MW 291.37 ($C_{17}H_{25}NO_3$); Mass spectrum EIMS m/z 291 (M)$^+$

EXAMPLE 24

4-(2-Methoxyphenyl)piperidine 1-t-Butoxycarbonyl-4-(2-methoxyphenyl)piperidine (120 mg, 0.41 mmol) was dissolved in methylene chloride (2 ml). Thereto was added trifluoroacetic acid (2 ml) and the resulting solution was stirred at a room temperature for 1 hour. The solvent was evaporated under a reduced pressure, and the thus obtained residue was mixed with ethyl acetate. This was washed with 1 N sodium hydroxide aqueous solution and saturated brine in that order, and then the solvent was evaporated under a reduced pressure to obtain 82 mg of the aforementioned compound of interest (0.43 mmol, 104% in yield).

$^1$H-NMR (CDCl$_3$) δ 1.56–1.68 (2 H, m), 1.78–1.88 (2 H, m), 2.74–2.83 (2 H, m), 3.08 (1 H, tt, J=3.4, 12 Hz), 3.15–3.22 (2 H, m), 3.83 (3 H, s), 6.86 (1 H, dd, J=1.1, 8.0 Hz), 6.94 (1 H, ddd, J=1.2, 7.6Hz), 7.15–7.22 (2 H, m); MW 191.28 ($C_{12}H_{17}NO$); Mass spectrum EIMS m/z 191 (M)$^+$

EXAMPLE 25

4-(2-Methoxyphenyl)-1,2,3,6-tetrahydropyridine 1-t-Butoxycarbonyl-4-hydroxy-4-(2-methoxyphenyl) piperidine (240 mg, 0.78 mmol) was dissolved in methylene chloride (4 ml). Thereto was added trifluoroacetic acid (4 ml) and the resulting solution was stirred at room temperature for 1 hour. The solvent was evaporated under a reduced pressure, and ethyl acetate was added to the thus obtained residue. This was washed with 1 N sodium hydroxide aqueous solution and saturated brine in that order, and then the solvent was evaporated under a reduced pressure to obtain 150 mg of the aforementioned compound of interest (0.78 mmol, 100% in yield).

$^1$H-NMR (CDCl$_3$) δ 2.43–2.48 (2 H, m), 3.06–3.10 (2 H, m), 3.50–3.54 (2 H, m), 3.81 (3 H, s), 5.79–5.82 (1 H, m), 6.87 (1 H, dd, J=1.1, 8.4 Hz), 6.92 (1 H, ddd, J=7.3, 7.6 Hz), 7.15 (1 H, dd, J=1.9 Hz), 7.23 (1 H, ddd); MW 189.26 ($C_{12}H_{15}NO$); Mass spectrum EIMS m/z 189 (M)$^+$

EXAMPLE 26

2a-[4-{4-(2-Methoxyphenyl)piperidyl}butyl]-2a,3,4, 5-tetrahydrobenz[cd]indole-2(1H)-one This compound was synthesized in the same manner as described in Example 5, except that 4-(2-methoxyphenyl) piperidine was used in stead of 4-(2-methoxyphenyl) piperazine (yield, 78%).

$^1$H-NMR (CDCl$_3$) δ 1.02–1.16 (1 H, m), 1.28–1.59 (3 H, m), 1.75–1.93 (8 H, m), 2.07–2.20 (4 H, m), 2.30–2.41 (2 H, m), 2.60–2.70 (1 H, m), 2.80–3.11 (4 H, m), 3.81 (3 H, s), 6.67 (1 H, d, J=7.8 Hz), 6.79–6.94 (3 H, m), 7.10–7.22 (3 H, m), 7.40 (1 H, br s); MW 418.58 ($C_{27}H_{34}N_2O_2$); Mass spectrum EISM m/z 418 (M)$^+$ The thus obtained free compound was dissolved in hydrochloric acid-saturated methanol to obtain its hydrochloric acid salt.

MW 455.04 ($C_{27}H_{35}ClN_2O_2$); Mass spectrum EIMS m/z 418 (M–HCl)$^+$

EXAMPLE 27

2a-[4-{4-(2-Methoxyphenyl)-1,2,3 6-tetrahydropyridyl}butyl]-2a,3,4,5-tetrahydrobenz[cd] indole-2(1H)-one This compound was synthesized in the same manner as described in Example 5, except that 4-(2-methoxyphenyl)-1,2,3,6-tetrahydropyridine was used in stead of 4-(2-methoxyphenyl)piperazine (yield, 77%).

$^1$H-NMR (CDCl$_3$) δ 1.03–1.17 (1 H, m), 1.30–1.57 (4 H, m), 1.78–1.94 (3 H, m), 2.07–2.20 (2 H, m), 2.30–2.43 (2 H, m), 2.50–2.70 (2 H, m), 2.80–2.91 (1 H, m), 3.04–3.11 (2 H, m), 3.79 (3 H, s), 5.71–5.76 (1 H, m), 6.67 (1 H, d, J=7.4 Hz), 6.79–6.94 (3 H, m), 7.09–7.24 (3 H, m), 7.44 (1 H, br s); MW 416.57 ($C_{27}H_{32}N_2O_2$); Mass spectrum EISM m/z 416 (M)$^+$ The thus obtained free compound was dissolved in hydrochloric acid-saturated methanol to obtain its hydrochloric acid salt.

MW 453.03 ($C_{27}H_{35}ClN_2O_2$); Mass spectrum EIMS m/z 416 (M–HCl)$^+$

EXAMPLE 28

2a-(4-Pentenyl)-2a,3,4 5-tetrahydrobenz[cd]indole-2 (1H)-one 2a,3,4,5-Tetrahydrobenz[cd]indole-2(1H) -one (4.0 g, 23 mmol) was dissolved in anhydrous N,N-dimethylformamide (100 ml). Thereto was added sodium hydride (760 mg, 190 mmol), and the resulting solution was stirred at 0° C. for 1 hour. The reaction solution was mixed with 1-bromopentene (3.8 g, 25 mmol) and stirred at –40° C. for 2 hours. The reaction solution was mixed with ethyl acetate, water and hydrochloric acid (1 N). The reaction product was extracted with ethyl acetate, washed with saturated brine and dried with anhydrous sodium sulfate. Then the compound obtained by the evaporation of the solvent under a reduced pressure was separated and purified by a silica gel column chromatography to obtain 2.7 g of the title compound (11 mmol, 49% in yield).

$^1$H-NMR (CDCl$_3$) δ 1.05–1.22 (1 H, m), 1.31–1.47 (2 H, m), 1.73–1.89 (3 H, m), 1.89–2.01 (2 H, m), 2.06–2.19 (2 H, m), 2.59–2.69 (1 H, m), 2.79–2.89 (1 H, m), 4.87–4.95 (2 H, m), 5.68 (1 H, m), 6.67 (1 H, d, J=7.8 Hz), 6.80 (1 H, d, J=7.8 Hz), 7.11 (1 H, dd), 7.49 (1 H, br s); MW 241.33 ($C_{16}H_{19}NO$); Mass spectrum EI m/z 241 (M)$^+$

EXAMPLE 29

2a-(3-Formylpropyl)-2a,3,4,5-tetrahydrobenz[cd] indole-2(1H)-one

In a shaded container, 2a-(4-pentenyl)-2a,3,4,5-tetrahydrobenz[cd]indole-2(1H)-one (1.3 g, 5.3 mmol) and N-methylmorpholine oxide (1.9 g, 16 mmol) were dissolved in a mixed solvent of 1,4-dioxane (20 ml) and water (10 ml), and the resulting solution was mixed with osmium tetroxide (4% aqueous solution 3.4 ml, 0.53 mmol) and stirred at a room temperature for 2 hours. The reaction solution was mixed with water (80 ml), and then the reaction product was extracted with ethyl acetate, washed with saturated brine and dried with anhydrous sodium sulfate. Then the solvent was evaporated under a reduced pressure. The thus obtained residue was dissolved in a mixed solvent of 1,4-dioxane (20 ml) and water (10 ml). The resulting solution was mixed with sodium periodate (2.6 g, 12 mmol) and stirred for 2.5 hours as such. Water (100 ml) was added to the reaction solution, and the reaction product was extracted with ethyl acetate, washed with saturated brine and dried with anhydrous sodium sulfate. By evaporating the solvent from the resulting extract under a reduced pressure, 1.3 g of the title compound was obtained (5.3 mmol, 100% in yield).

$^1$H-NMR (CDCl$_3$) δ 1.21–1.50 (2 H, m), 1.55–1.70 (1 H, m), 1.75–1.91 (1 H, m), 2.06–2.19 (2 H, m), 2.27–2.42 (2 H, m), 2.60–2.70 (1 H, m), 2.79–2.90 (1 H, m), 6.68 (1 H, d, J=7.8 Hz), 6.81 (1 H, d, J=7.8 Hz), 7.12 (1 H, dd), 7.56 (1 H, br s), 9.66 (1 H, s); MW 243.31 (C15H$_{17}$NO$_2$); Mass spectrum EI m/z 243 (M)$^+$

EXAMPLE 30

2a-[4-{4-(4-Methylphenyl)-1,2,3 6-tetrahydropyridyl}butyl]-2a,3,4,5-tetrahydrobenz[cd] indole-2(1H)-one 2a-(3-Formylpropyl)-2a,3,4,5-tetrahydrobenz[cd]indole-2(1H)-one (260 mg, 1.1 mmol), 4-(4-methylphenyl)-1,2,3, 6-tetrahydropyridine (240 mg, 1.1 mmol), acetic acid (625 mg, 10.4 mmol) and sodium triacetoxyborate (441 mg, 2.1 mmol) were stirred in 1,2-dichloroethane (3 ml) at room temperature for 4 hours. The reaction solution was mixed with ethyl acetate (60 ml), washed with sodium hydroxide aqueous solution (1 N) and saturated brine and dried with anhydrous sodium sulfate. Then the compound obtained by the evaporation of the solvent under a reduced pressure was separated and purified by a silica gel column chromatography to obtain 460 mg of the title compound (1.1 mmol, 100% in yield).

$^1$H-NMR (CDCl$_3$) δ 1.04–1.16 (1 H, m), 1.29–1.39 (2 H, m), 1.51–1.64 (2 H, m), 1.77–1.92 (3 H, m), 2.04–2.18 (2 H, m), 2.33 (3 H, m), 2.51–2.69 (3 H, m), 2.80–2.90 (3 H, m), 3.27–3.34 (2 H, m), 5.95 (1 H, m), 6.67 (1 H, d, J=7.6 Hz), 6.80 (1 H, d, J=7.9 Hz), 7.09–7.14 (3 H, m), 7.23–7.28 (2 H, m); MW 418.58 (C$_{27}$H$_{34}$N$_2$O$_2$); Mass spectrum EI m/z 418 (M)$^+$ The thus obtained free compound was dissolved in hydrochloric acid-saturated methanol to obtain its hydrochloric acid salt.

MW (C$_{27}$H$_{33}$ClN$_2$O) 437.03; Mass spectrum EI m/z 400 (M−HCl)$^+$

EXAMPLE 31

2a-[4-{4-(4-Fluorophenyl)-1,2,3,6-tetrahydropyridyl}butyl]-2a,3,4,5-tetrahydrobenz[cd]indole-2(1H)-one This compound was synthesized in the same manner as described in Example 30, except that 4-(4-fluorophenyl)-1,2,3,6-tetrahydropyridine was used in stead of 4-(4-methylphenyl)-1,2,3,6-tetrahydropyridine (yield, 93%).

$^1$H-NMR (CDCl$_3$) δ 1.04–1.19 (1 H, m), 1.29–1.56 (4 H, m), 1.74–1.93 (3 H, m), 2.06–2.11 (2 H, m), 2.29–2.41 (2 H, m), 2.45–2.53 (2 H, m), 2.58–2.69 (3 H, m), 2.80–2.89 (1 H, m), 3.04–3.09 (2 H, m), 5.69 (1 H, m), 6.67 (1 H, d, J=7.6 Hz), 6.80 (1 H, d, J=7.8 Hz), 6.94–7.01 (2 H, m), 7.11 (1 H, dd), 7.28–7.34 (2 H, m), 7.69 (1 H, s); MW 404.53 (C$_{26}$H$_{29}$N$_2$O$_2$F); Mass spectrum EI m/z 404 (M)$^+$

EXAMPLE 32

1-Phenyl-2-methylpiperazine 1-(4-chlorophenyl)-2-methylpiperazine (300 mg, 1.4 mmol) was dissolved in methanol (3 ml), and the resulting solution was mixed with palladium carbon (150 mg) and stirred at a room temperature for 21 hours in an atmosphere of hydrogen. The reaction solution was filtered, and the thus obtained residue was thoroughly washed with ethanol. The washed solution and filtrate were combined, and the solvent was evaporated therefrom under a reduced pressure to obtain 260 mg of the title compound (1.4 mmol, 100% in yield).

$^1$H-NMR (CDCl$_3$) δ 1.11 (1 H, d, J=6.5 Hz), 3.06–3.12 (1 H, m), 3.30–3.46 (5 H, m), 3.78–3.85 (1 H, m), 7.01–7.09 (3 H, m), 7.29–7.34 (2 H, m); MW 176.26 (C$_{11}$H$_{16}$N$_2$); Mass spectrum EI m/z 176 (M)$^+$

EXAMPLE 33

2a-[4-{4-(4-Phenyl-3-methyl-piperazinyl}butyl]-2a,3,4,5-tetrahydrobenz[cd]indole-2(1H)-one This compound was synthesized in the same manner as described in Example 5, except that 1-phenyl-2-methylpiperazine was used in stead of 4-(2-methoxyphenyl)piperazine (yield, 65%).

$^1$H-NMR (CDCl$_3$) δ 0.96–1.18 (4 H, m), 1.29–1.50 (4 H, m), 1.76–1.92 (3 H, m), 2.07–2.41 (6 H, m), 2.47–2.53 (1 H, m), 2.60–2.72 (2 H, m), 2.80–2.90 (1 H, m), 3.01–3.10 (1 H, m), 3.11–3.19 (1 H, m), 3.72–3.80 (1 H, m), 6.67 (1 H, d, J=7.6 Hz), 6.78–6.94 (4 H, m), 7.11 (1 H, dd), 7.20–7.28 (2 H, m), 7.74 and 7.75 (1 H, s); MW 403.57 (C$_{26}$H$_{33}$N$_3$O); Mass spectrum EI m/z 403 (M)$^+$ The thus obtained free compound was dissolved in hydrochloric acid-saturated methanol to obtain its hydrochloric acid salt.

MW (C$_{26}$H$_{34}$ClN$_3$O) 440.03; Mass spectrum EI m/z 403 (M−HCl)$^+$

EXAMPLE 34

1-(2-Cyanophenyl)1piperazine

2-Aminobenzonitrile (6.1 g, 52 mmol) and bis(2-chloroethyl)amine hydrochloride (10 g, 57 mmol) were dissolved in xylene (100 ml) and then stirred at 140 to 150° C. for 4 days. The reaction solution was mixed with sodium hydroxide aqueous solution (1 N), and the reaction product was extracted with ethyl acetate, washed with saturated brine and dried with sodium sulfate. Then the compound obtained by the evaporation of the solvent under a reduced pressure was separated and purified by a silica gel column chromatography to obtain 2.3 g of the title compound (13 mmol, 24% in yield).

$^1$H-NMR (CDCl$_3$) δ 3.36–3.11 (4 H, m), 3.17–3.21 (4 H, m), 6.98–7.03 (2 H, m), 7.46–7.51 (1 H, m), 7.55–7.58 (1 H, m); MW 187.25 (C$_{11}$H$_{13}$N$_3$); Mass spectrum EI m/z 187 (M)$^+$

EXAMPLE 35

2a-[4-{4-(2-Cyanophenyl)piperazinyl}butyl]-2a,3,4,5-tetrahydrobenz[cd]indole-2(1H)-one This compound was synthesized in the same manner as described in Example 30, except that 1-(2-cyanophenyl)piperazine was used in stead of 4-(4-methoxyphenyl)-1,2,3,6-tetrahydropyridine (yield, 97%).

$^1$H-NMR (CDCl$_3$) δ 1.03–1.14 (1 H, m), 1.30–1.50 (4 H, m), 1.75–1.92 (3 H, m), 2.07–2.19 (2 H, m), 2.28–2.38 (2 H, m), 2.55–2.70 (5 H, m), 2.80–2.90 (1 H, m), 3.17–3.22 (4 H, m), 6.67 (1 H, d, J=7.6 Hz), 6.81 (1 H, d, J=7.8 Hz), 6.96–7.00 (2 H, m), 7.12 (1 H, dd), 7.36 (1 H, br s), 7.44–7.49 (1 H, m), 7.54 (1 H, dd, J=1.5, 7.8 Hz); MW 414.55 (C$_{26}$H$_{30}$N$_4$O); Mass spectrum EI m/z 414 (M)$^+$ The thus obtained free compound was dissolved in hydrochloric acid-saturated methanol to obtain its hydrochloric acid salt.

MW (C$_{26}$H$_{13}$ClN$_4$O) 451.01; Mass spectrum EI m/z 414 (M−HCl)$^+$

EXAMPLE 36

1-(2-Carbamoylphenyl)piperazine 1-(2-Cyanophenyl)piperazine (1.8 g, 9.8 mmol) was dissolved in 90% sulfuric acid aqueous solution (20 ml) and stirred at a room temperature for 24 hours. The reaction solution was slowly added dropwise to a mixture of ice (75 g) and 28% aqueous ammonia (75 ml), and the reaction product was extracted with chloroform. The extract was washed with saturated brine and dried with sodium sulfate. Then the compound obtained by the evaporation of the solvent under a reduced pressure was separated by an aluminum column chromatography to obtain colorless crystals. By further recrystallizing the thus obtained crystals from ethyl acetate, 680 mg of the title compound was obtained (3.1 mmol, 32% in yield).

$^1$H-NMR (CDCl$_3$) δ 2.98–3.02 (4 H, m), 3.04–3.08 (4 H, m), 5.82 (1 H, br s), 7.21–7.25 (2 H, m), 7.45–7.50 (1 H, m), 8.15–8.18 (1 H, m), 9.57 (1 H, br s); MW 205.26 (C$_{11}$H$_{15}$N$_3$O); Mass spectrum EI m/z 205 (M)$^+$

EXAMPLE 37

2a-[4-{4-(2-Carbamoylphenyl piperazinyl}butyl]-2a, 3,4,5-tetrahydrobenz[cd]indole-2(1H)-one This compound was synthesized in the same manner as described in Example 30, except that 1-(2-carbamoylphenyl) piperazine was used in stead of 4-(4-methylphenyl)-1,2,3, 6-tetrahydropyridine (yield, 98%).

$^1$H-NMR (CDCl$_3$) δ 1.07–1.17 (1 H, m), 1.31–1.49 (3 H, m), 1.75–1.92 (4 H, m), 2.05–2.14 (2 H, m), 2.50–2.70 (5 H, m), 2.80–2.90 (1 H, m), 2.98–3.03 (4 H, m), 5.85 (1 H, br s), 6.68 (1 H, d, J=7.8 Hz), 7.12 (1 H, dd), 7.19–7.28 (2 H, m), 7.45–7.60 (2 H, m), 9.51 (1 H, br s); MW 432.57 (C$_{26}$H$_{32}$N$_4$O$_2$); Mass spectrum EI m/z 432 (M)$^+$ The thus obtained free compound was dissolved in hydrochloric acid-saturated methanol to obtain its hydrochloric acid salt.

MW (C$_{26}$H$_{33}$ClN$_4$O$_2$) 469.03; Mass spectrum EI m/z 432 (M–HCl)$^+$

EXAMPLE 38

1-t-Butoxycarbonyl-4-(2-carbamoylphenyl) piperazine 1-(2-Carbamoylphenyl)piperazine (300 mg, 1.5 mmol) was dissolved in water (2 ml) and 1,4-dioxane (2 ml) The resulting solution was mixed with sodium bicarbonate (250 mg, 2.9 mmol) and di-t-butyl carbonate (480 mg, 2.2 mmol), and then stirred at a room temperature for 4 hours. The reaction solution was mixed with water (20 ml), and the reaction product was extracted with chloroform (80 ml) and washed with water and saturated brine. Then the solvent was evaporated under a reduced pressure to obtain colorless crystals. Thereafter, the crystals were washed with hexane and then dried to obtain 430 mg of the title compound (1.4 mmol, 96% in yield).

$^1$H-NMR (CDCl$_3$) δ 1.49 (9 H, s), 2.95–3.02 (4 H, m), 3.58–3.64 (4 H, m), 5.75 (1 H, br s), 7.25 (1 H, m), 7.47 (1 H, ddd, J=7.7 Hz), 8.16 (1 H, dd, J=7.8, 1.7 Hz), 9.29 (1 H, br s); MW 305.35 (C$_{16}$H$_{23}$N$_3$O$_3$); Mass spectrum EI m/z 305 (M)$^+$

EXAMPLE 39

1-t-Butoxycarbonyl-4-(2-N,N-dimethylcarbamoylphenyl)piperazine 1-t-Butoxycarbonyl-4-(2-carbamoylphenyl)piperazine (420 mg, 1.4 mmol) was dissolved in anhydrous N,N-dimethylformamide (10 ml). Thereto was added sodium hydride (content 60%, 120 mg, 2.9 mmol) and the resulting solution was stirred at 50° C. for 1 hour. The reaction solution was returned to a room temperature, mixed with iodomethane (410 mg, 2.9 mmol) and again stirred for 2.5 hours. The reaction solution was mixed with ethyl acetate, washed with water and saturated brine and dried with anhydrous sodium sulfate. Then the solvent was evaporated under a reduced pressure to obtain colorless crystals. Thereafter, the thus obtained crystals were washed with hexane and then dried to obtain 370 mg of the title compound (1.1 mmol, 80% in yield).

$^1$H-NMR (CDCl$_3$) δ 1.47 (9 H, s), 2.75–2.86 (5 H, m), 3.12 (3 H, s), 3.15–3.23 (2 H, m), 3.38–3.59 (4 H, m), 6.98 (1 H, dd, J=7.6 Hz), 7.08 (1 H, ddd, J=7.7, 7.6, 0.98 Hz), 7.25–7.28 (1 H, m), 7.33 (1 H, ddd, J=1.7 Hz); MW 333.43 (C$_{18}$H$_{27}$N$_3$O$_3$); Mass spectrum EI m/z 333 (M)$^+$

EXAMPLE 40

2a-[4-{4-(2-N,N-Dimethylcarbamoylphenyl) piperazinyl}butyl]-2a,3,4,5-tetrahydrobenz[cd] indole-2(1H)-one 1-t-Butoxycarbonyl-4-(2-N,N-dimethylcarbamoylphenyl)-piperazine (370 mg, 1.1 mmol) was dissolved in hydrochloric acid-saturated methanol (4 ml) and stirred at a room temperature for 5 hours. After evaporation of the solvent under a reduced pressure, the thus obtained residue was washed with isopropyl ether and thoroughly dried to obtain 340 mg of colorless powder. Thereafter, 260 mg (0.57 mmol, 88% in yield) of the title compound was obtained by carrying out its synthesis in the same manner as described in Example 30, except that a 190 mg portion of the just obtained powder was used in stead of 4-(4-methylphenyl)-1,2,3,6-tetrahydropyridine. 1H-NMR (CDCl$_3$) δ 1.03–1.14 (1 H, m), 1.30–1.46 (4 H, m), 1.74–1.91 (3 H, m), 2.06–2.16 (2 H, m), 2.20–2.32 (2 H, m), 2.37–2.48 (4 H, m), 2.60–2.70 (1 H, m), 2.78–2.89 (6 H, m), 3.10 (3 H, s), 3.13–3.25 (2 H, m), 6.66 (1 H, d, J=7.6 Hz), 6.80 (1 H, d, J=7.8 Hz), 6.96 (1 H, d, J=8.0 Hz), 7.03 (1 H, ddd, J=0.73, 6.9 Hz), 7.11 (1 H, dd), 7.22–7.35 (3 H, m); MW 460.62 (C$_{28}$H$_{36}$N$_4$O$_2$); Mass spectrum EI m/z 460 (M)$^+$

EXAMPLE 41

1-(3-Cyanophenyl)piperazine

3-Aminobenzonitrile (6.1 g, 52 mmol) and bis(2-chloroethyl)amine hydrochloride (10 g, 57 mmol) were dissolved in xylene (100 ml), and the resulting solution was stirred at 150 to 160° C. for 5 hours. Supernatant fluid of the reaction solution was discarded, the remaining residue was dissolved in sodium hydroxide aqueous solution (1 N) and then the reaction product was extracted therefrom with ethyl acetate. The extract was washed with saturated brine, and then the compound obtained by the evaporation of the solvent under a reduced pressure was separated and purified by a silica gel column chromatography to obtain 3.2 g of the title compound (17 mmol, 34% in yield). A portion of the thus obtained compound was made into hydrochloric acid salt by treating it with hydrochloric acid-saturated methanol.

$^1$H-NMR (CDCl$_3$) δ 3.02–3.06 (4 H, m), 3.16–3.20 (4 H, m), 7.07–7.14 (3 H, m), 7.20–7.34 (1 H, m); MW 187.25 (C$_{11}$H$_{13}$N$_3$); Mass spectrum EI m/z 187 (M)$^+$

EXAMPLE 42

2a-[4-{4-(3-Cyanophenyl)piperazinyl}butyl]-2a,3,4, 5-tetrahydrobenz[cd]indole-2(1H)-one This compound was synthesized in the same manner as described in Example 30, except that 1-(3-cyanophenyl)-piperazine was used in stead of 4-(4-methylphenyl)-tetrahydropyridine (yield, 82%).

$^1$H-NMR (CDCl$_3$) δ 1.04–1.16 (1 H, m), 1.29–1.39 (2 H, m), 1.51–1.64 (2 H, m), 2.04–2.18 (2 H, m), 2.33 (3 H, s), 2.51–2.69 (5 H, m), 2.80–2.90 (3 H, m), 3.27–3.34 (2 H, m), 5.95 (1 H, m), 6.67 (1 H, d, J=7.6 Hz), 6.80 (1 H, d, J=7.9

Hz), 7.09–7.14 (3 H, m), 7.23–7.28 (2 H, m), 7.63 (1 H, br s); MW 414.55 ($C_{26}H_{30}N_4O$); Mass spectrum EI m/z 414 $(M)^+$

EXAMPLE 43

1-(3-Carbamoylphenyl)piperazine 1-(3-Cyanophenyl)piperazine (1.6 g, 8.3 mmol) was dissolved in 90% sulfuric acid aqueous solution (17 ml) and stirred at a room temperature for 2 days. The reaction solution was slowly added drbpwise to a mixture consisting of ice (65 g) and 28% aqueous ammonia (65 ml), and the reaction product was extracted with chloroform. The resulting extract was washed with saturated brine and dried with sodium sulfate, and then the solvent was evaporated under a reduced pressure to obtain 990 mg of the title compound (4.9 mmol, 58% in yield).

$^1$H-NMR ($CDCl_3$) δ 3.02–3.04 (4 H, m), 3.19–3.22 (4 H, m), 5.68 (1 H, br s), 6.08 (1 H, br s), 7.06–7.09 (1 H, m), 7.16–7.18 (1 H, m), 7.31 (1 H, dd, J=7.8, 8.0 Hz), 7.44–7.45 (1 H, m); MW 205.26 ($C_{11}H_{15}N_3O$); Mass spectrum EI m/z 205 $(M)^+$

EXAMPLE 44

2a-[4-{4-(3-Carbamoylphenyl)piperazinyl}butyl]-2a, 3,4,5-tetrahydrobenz[cd]indole-2(1H)-one This compound was synthesized in the same manner as described in Example 30, except that 1-(3-carbamoylphenyl) piperazine was used in stead of 4-(4-methylphenyl)-1,2,3, 6-tetrahydropyridine (yield, 95%).

$^1$H-NMR ($CDCl_3$) δ 0.92–1.05 (1 H, m), 1.10–1.28 (2 H, m), 1.30–1.40 (2 H, m), 1.67–1.77 (3 H, m), 2.01–2.15 (1 H, m), 2.15–2.27 (2 H, m), 2.40–2.47 (4 H, m), 2.52–2.62 (1 H, m), 2.75–2.85 (1 H, m), 3.09–3.17 (4 H, m), 6.60 (1 H, d, J=7.6 Hz), 6.71 (1 H, d, J=7.8 Hz), 7.00–7.07 (2 H, m), 7.20–7.29 (3 H, m), 7.39 (1 H, br s), 7.87 (1 H, be s), 10.07 (1 H, br s); MW 432.57 ($C_{26}H_{32}N_4O_2$); Mass spectrum EI m/z 432 $(M)^+$

EXAMPLE 45

2a-[4-{4-(2-Hydroxyphenyl)piperazinyl}butyl]-2a,3, 4,5-tetrahydrobenz[cd]indole-2(1H)-one 2a-[4-{4-(2-Methoxyphenyl)piperazinyl}butyl]-2a,3,4,5-tetrahydrobenz[cd]indole-2(1H) -one (100 mg, 0.24 mmol) was dissolved in benzene (2 ml) to which was subsequently added dropwise boron tribromide (240 mg, 0.96 mmol), and the resulting mixture was stirred at room temperature for 2 hours and then at 60° C. for 24 hours. The reaction solution was mixed with methanol and ethyl acetate, washed with water and saturated brine and dried with anhydrous sodium sulfate. Then the solvent was evaporated under a reduced pressure to obtain 57 mg of the title compound (0.14 mmol, 59% in yield).

$^1$H-NMR ($CD_3OD$) δ 1.07–1.20 (1 H, m), 1.20–1.40 (2 H, m), 1.61–1.76 (2 H, m), 1.80–1.96 (3 H, m), 2.00–2.10 (1 H, m), 2.12–2.25 (1 H, m), 2.62–2.71 (1 H, m), 2.82–2.93 (1 H, br s), 2.97–3.13 (4 H, m), 3.18–3.27 (2 H, m), 3.43–3.60 (4 H, m), 6.70 (1 H, d, J=7.6 Hz), 6.79–6.85 (3 H, m), 6.93–7.01 (2 H, m), 7.12 (1 H, dd, J=7.8 Hz); MW 405.54 ($C_{25}H_{31}N_3O_2$); Mass spectrum EI m/z 405 $(M)^+$

EXAMPLE 46

1-(2-Bromoethyl)-2a,3,4,5-tetrahydrobenz[cd] indole-2(1H)-one 2a,3,4,5-Tetrahydrobenz[cd]indole-2(1H) -one (3.46 g, 20mmol) was dissolved in anhydrous N,N-dimethylformamide (20 ml). Thereto was added sodium hydride (0.8 g, 20 mmol), and the resulting solution was stirred at room temperature for 1 hour. The reaction solution was mixed with 1,2-dibromoethane (10 ml, 115 mmol) and again stirred for 1 hour. The reaction solution was extracted by adding 100 ml of ethyl acetate and 100 ml of water, and the resulting ethyl acetate layer was separated, washed with water and dried with anhydrous sodium sulfate. Then the compound obtained by the evaporation of the solvent under a reduced pressure was crystallized from a dimethylformamide-water mixture to obtain 1.9 g of the title compound (34% in yield).

$^1$H-NMR ($CDCl_3$) δ 1.39 (1 H, m), 1.92 (1 H, m), 2.17 (2 H, m), 2.34 (1 H, m), 2.46 (1 H, m), 2.69 (1 H, m), 2.88 (1 H, m), 3.18 (1 H, m), 2.47 (1 H, m), 6.75 (1 H, d, J=7.4 Hz), 6.82 (1 H, d, J=7.8 Hz), 7.15 (1 H, dd), 8.51 (1 H, br s); Mass spectrum EI m/z 279:281=1:1 $(M)^+$

EXAMPLE 47

2a-[2-{4-(2-Methoxyphenyl)piperazinyl}ethyl]-2a,3, 4,5-tetrahydrobenz[cd]indole-2(1H)-one 2a-(2-Bromoethyl)-2a,3,4,5-tetrahydrobenz[cd]indole-2 (1H)-one (140 mg, 0.5 mmol), 4-(2-methoxyphenyl) piperazine (148 mg, 0.77 mmol) and potassium carbonate (138 mg, 1 mmol) were stirred in anhydrous N,N-dimethylformamide (5 ml) at room temperature for 2 hours. The reaction solution was mixed with ethyl acetate (50 ml) and water (50 ml). The ethyl acetate layer was washed with water and dried with anhydrous sodium sulfate. Then the compound obtained by the evaporation of the solvent under a reduced pressure was separated and purified by a silica gel column chromatography to obtain 63 mg of the title compound (32% in yield).

The thus obtained free compound was dissolved in hydrochloric acid-saturated methanol to obtain its hydrochloric acid salt.

$^1$H-NMR ($CDCl_3$-$D_2O$) δ 1.31 (1 H, m), 1.75 (1 H, m), 2.08–2.30 (4 H, m), 2.45–3.02 (8 H, m), 3.17 (4 H, m), 3.83 (3 H, s), 6.69 (1 H, d), 6.79–7.03 (5 H, m), 7.12 (1 H, dd); Mass spectrum EI m/z 391 $(M)^+$

EXAMPLE 48

2a-[2-(4-Phenylpiperazinyl)ethyl]-2a,3,4,5-tetrahydrobenz[cd]indole-2(1H)-one

Using 2a-(2-bromoethyl)-2a,3,4,5-tetrahydrobenz[cd] indole-2(1H)-one (280 mg, 1 mmol), 344 mg (1 mmol) of 4-phenylpiperazine, 0.3 g of potassium carbonate and anhydrous N,N-dimethylformamide (10 ml), 37 mg (yield, 9.7%) of the title compound was obtained in the same manner as described in Example 47.

$^1$H-NMR ($CDCl_3$) δ 1.26 (1 H, m), 1.83 (1 H, m), 2.01 (2 H, m), 2.27 (3 H, m), 2.24 (2 H, m), 2.45 (4 H, m), 2.63 (1 H, m), 2.63 (1 H, m), 3.05 (4 H, m), 6.68 (1 H, d), 6.81–6.91 (4 H, m), 7.13 (1 H, dd), 7.23 (1 H, br s); Mass spectrum EI m/z 361 $(M)^+$

EXAMPLE 49

2a-[3-(4-Phenylpiperazinyl)propyl]-2a,3,4,5-tetrahydrobenz-[cd]indole-2(1H)-one

Using 2a-(3-bromopropyl)-2a,3,4,5-tetrahydrobenz[cd] indole-2(1H)-one (140 mg, 0.5 mmol), 4-phenylpiperazine (162 mg, 1 mmol), potassium carbonate (210 mg, 1.5 mmol)

and anhydrous N,N-dimethylformamide (6 ml), 95 mg (yield, 51%) of the title compound was obtained in the same manner as described in Example 47.

$^1$H-NMR (CDCl$_3$) δ 1.34 (3 H, m), 1.86 (3 H, m), 2.12 (2 H, m), 2.29 (2 H, m), 2.50 (4 H, m), 2.65 (1 H, m), 2.83 (1 H, m), 3.16 (4 H, m), 6.68 (1 H, d), 6.80–6.95 (4 H, m), 7.12 (1 H, dd), 7.23–7.28 (3 H, m), 7.43 (1 H, br s); Mass spectrum EI m/z 375 (M)$^+$

EXAMPLE 50

2a-[4-{4-(4-Chlorophenyl)-4-hydroxy-piperidyl}butyl]-2a,3,4,5-tetrahydrobenz[cd]indole-2(1H)-one 2a-(4-bromobutyl)-2a,3,4,5-tetrahydrobenz[cd]indole-2(1H)-one (390 mg, 1.3 mmol), 4-(4-chlorophenyl)-4-hydroxypiperidine (290 mg, 1.4 mmol) and potassium carbonate (260 mg, 1.9 mmol) were stirred in anhydrous N,N-dimethylformamide (10 ml) at 60° C. for 3 hours. The solvent was evaporated under a reduced pressure, and the thus obtained residue was mixed with ethyl acetate and water. The reaction product was extracted with ethyl acetate, washed with saturated brine and dried with anhydrous sodium sulfate. Then the compound obtained by the evaporation of the solvent under a reduced pressure was separated and purified by a silica gel column chromatography to obtain 490 mg of the title compound (1.1 mmol, 90% in yield).

$^1$H-NMR (CDCl$_3$) δ 1.01–1.16 (1 H, m), 1.27–1.40 (2 H, m), 1.41–1.58 (1 H, m), 1.67–1.92 (6 H, m), 2.05–2.23 (4 H, m), 2.32–2.52 (4 H, m), 2.60–2.70 (1 H, m), 2.77–2.90 (3 H, m), 6.68 (1 H, d, J=8.0 Hz), 6.80 (1 H, d, J=7.6 Hz), 7.11 (1 H, dd), 7.30 (2 H, d, J=8.0 Hz), 7.42 (2 H, d), 7.68 (1 H, br s); MW 439.00 (C$_{26}$H$_{31}$ClN$_2$O$_2$); Mass spectrum EI m/z 438:440 (intensity ratio 3:1) (M)$^+$ The thus obtained free compound was dissolved in hydrochloric acid-saturated methanol to obtain its hydrochloric acid salt.

MW (C$_{26}$H$_{32}$Cl$_2$N$_2$O$_2$) 475.46; Mass spectrum EI m/z 438:440 (intensity ratio: 3:1) (M–HCl)$^+$

EXAMPLE 51

2a-[4-(4-Hydroxy-4-phenyl-piperidyl)butyl]-2a,3,4,5-tetrahydrobenz[cd]indole-2(1H)-one This compound was synthesized in the same manner as described in Example 50, except that 4-hydroxy-4-phenyl-piperidine was used in stead of 4-(4-chlorophenyl)-4-hydroxy-piperidine (yield, 99%).

$^1$H-NMR (CDCl$_3$) δ 1.02–1.15 (1 H, m), 1.28–1.91 (9 H, m), 2.05–2.20 (4 H, m), 2.25–2.43 (4 H, m), 2.59–2.69 (1 H, m), 2.71–2.90 (3 H, m), 6.67 (1 H, d, J=7.6 Hz), 6.81)1 H, d, J=7.6 Hz), 7.12 (1H, dd), 7.23–7.51 (6H, m); MW 404.55 (C$_{26}$H$_{32}$N$_2$O$_2$); Mass spectrum EI m/z 404 (M)$^+$ The thus obtained free compound was dissolved in hydrochloric acid-saturated methanol to obtain its hydrochloric acid salt.

MW (C$_{26}$H$_{33}$ClN$_2$O$_2$) 441.02; Mass spectrum ES m/z 405 (M–HCl+H)$^+$

EXAMPLE 52

2a-[4-(4-Cyano-4-phenyl-piperidyl)butyl]-2a,3,4,5-tetrahydrobenz[cd]indole-2(1H)-one This compound was synthesized in the same manner as described in Example 50, except that 4-cyano-4-phenyl-piperidine was used in stead of 4-(4-chlorophenyl)-4-hydroxy-piperidine (yield, 35%).

$^1$H-NMR (CDCl$_3$) δ 1.03–1.14 (1 H, m), 1.25–1.50 (4 H, m), 1.75–1.92 (3 H, m), 2.03–2.20 (6 H, m), 2.30–2.47 (4 H, m), 2.61–2.70 (1 H, m), 6.67 (1 H, d, J=7.6 Hz), 6.81 (1 H, d, J=7.6 Hz), 7.12 (1 H, dd), 7.23–7.51 (6 H, m); MW 413.56 (C$_{27}$H$_{31}$N$_3$O); Mass spectrum EI m/z 413 (M)$^+$ The thus obtained free compound was dissolved in hydrochloric acid-saturated methanol to obtain its hydrochloric acid salt.

MW (C$_{27}$H$_{32}$ClN$_3$O) 450.2; Mass spectrum PB m/z 414 (M–HCl+H)$^+$

EXAMPLE 53

1-t-Butoxycarbonyl-4-hydroxy-4-phenylpiperidine

4-Hydroxy-4-phenylpiperidine (1.0 g, 5.6 mmol) was dissolved in a mixed solvent of water (5 ml) and 1,4-dioxane (5 ml). Thereto were added sodium bicarbonate (950 mg, 11 mmol) and di-t-butyl dicarbonate (1.9 g, 8.5 mmol), and the resulting solution was stirred at a room temperature for 4 hours. The solvent was evaporated under a reduced pressure, and the thus obtained residue was mixed with dichloromethane and water. The reaction product was extracted with dichloromethane, washed with water and saturated brine and dried with anhydrous sodium sulfate. Then the material obtained by the evaporation of the solvent under a reduced pressure was thoroughly washed with hexane to obtain 1.5 g of the title compound (5.3 mmol, 94%).

$^1$H-NMR (CDCl$_3$) δ 1.48 (9 H, S), 1.70–1.77 (2 H, m), 1.91–2.08 (2 H, m), 3.18–3.32 (2 H, m), 3.92–4.15 (2 H, m), 7.26–7.30 (1 H, m), 7.37 (1 H, dd, J=6.1 Hz, 6.9 Hz), 7.37 (1 H, dd, J=6.1 Hz, 7.3 Hz), 7.47–7.49 (2 H, m); MW 277.36 (C$_{16}$H$_{23}$NO$_3$); Mass spectrum ES m/z 278 (M+H)$^+$

EXAMPLE 54

1-t-Butoxycarbonyl-4-methoxy-4-phenylpiperidine 1-t-Butoxycarbonyl-4-hydroxy-4-phenylpiperidine (300 mg, 1.1 mmol) was dissolved in tetrahydrofuran (9 ml). Thereto was added sodium hydride (43 mg, 1.1 mmol), and the resulting solution was stirred at a room temperature for 1 hour. The reaction solution was mixed with methyl iodide (0.1 ml, 1.6 mmol) and again stirred for 17 hours. The solvent was evaporated under a reduced pressure, and the thus obtained residue was mixed with ethyl acetate and water. The reaction product was extracted with ethyl acetate, washed with water and saturated brine and dried with anhydrous sodium sulfate. Then the compound obtained by the evaporation of the solvent under a reduced pressure was separated and purified by a silica gel column chromatography to obtain 240 mg of the title compound (0.82 mmol, 76% in yield).

$^1$H-NMR (CDCl$_3$) δ 1.47 (9 H, s), 1.77–1.92 (2 H, m), 1.95–2.07 (2 H, m), 3.17–3.10 (2 H, m), 3.83–4.06 (2 H, m), 7.25–7.40 (5 H, m); MW 291.39 (C$_{17}$H$_{25}$NO$_3$); Mass spectrum EI m/z 291 (M)$^+$

EXAMPLE 55

4-Methoxy-4-phenylpiperidine 1-t-Butoxycarbonyl-4-methoxy-4-phenylpiperidine (150 mg, 0.51 mmol) was dissolved in a mixed solvent of 1,4-dioxane (20 ml) and concentrated hydrochloric acid (10 ml). The resulting solution was stirred at 0° C. for a while and then gradually returned to a room temperature spending 1.5 hours. The reaction solution was neutralized by adding with sodium hydroxide aqueous solution (1 N), and then the solvent was evaporated under a reduced pressure. The thus obtained residue was mixed with ethyl acetate and water, the reaction product was extracted with ethyl acetate, washed with water and saturated brine and dried with anhydrous sodium sulfate. Then the solvent was evaporated under a reduced pressure was separated and purified by a silica gel column chromatography to obtain 49 mg of the title compound (0.25 mmol, 49% in yield).

$^1$H-NMR (CDCl$_3$) δ 1.84–1.92 (2 H, m), 1.99–2.05 (2 H, m), 2.90–2.99 (5 H, m), 3.03–3.11 (2 H, m), 7.24–7.43 (5 H, m); MW 191.27 (C$_{12}$H$_{17}$NO); Mass spectrum EI m/z 191 (M)$^+$

EXAMPLE 56

2a-[4-(4-Methoxy-4-phenyl-piperidyl)butyl]-2a,3,4,5-tetrahydrobenz[cd]indole-2(1H)-one This compound was synthesized in the same manner as described in Example 50, except that 4-methoxy-4-phenylpiperidine was used in stead of 4-(4-chlorophenyl)-4-hydroxy-piperidine (yield, 96%).

$^1$H-NMR (CDCl$_3$) δ 1.04–1.16 (1 H, m), 1.25–1.31 (2 H, m), 1.36–1.50 (1 H, m), 1.76–1.92 (4 H, m), 1.99–2.20 (6 H, m), 2.38–2.53 (4 H, m), 2.60–2.69 (1 H, m), 2.77–2.89 (3 H, m), 2.95 (3 H, s), 6.67 (1 H, d, J=7.4 Hz), 6.80 (1 H, d, J=7.8 Hz), 7.11 (1 H, dd), 7.24–7.40 (5 H, m), 7.43 (1 H, br s); MW 418.58 (C$_{27}$H$_{34}$N$_2$O$_2$); Mass spectrum EI m/z 418 (M)$^+$ The thus obtained free compound was dissolved in hydrochloric acid-saturated methanol to obtain its hydrochloric acid salt.

MW (C$_{27}$H$_{35}$ClN$_2$O$_2$) 455.04; Mass spectrum EI m/z 418 (M–HCl)$^+$

EXAMPLE 57

1-Benzyl-4-phenyl-1,2,3,6-tetrahydropyridine 1,2,3,6-Tetrahydro-4-phenylpyridine (410 mg, 2.6 mmol), benzaldehyde (300 mg, 2.9 mmol), sodium triacetoxyborate (1.1 g, 5.2 mmol) and acetic acid (1.5 ml, 26 mmol) were stirred in dichloroethane at a room temperature for 14 hours. To the reaction solution was added ethyl acetate, and the resulting solution was washed with sodium hydroxide aqueous solution (1 N) and saturated brine and dried with anhydrous sodium sulfate. Then the solvent was evaporated under a reduced pressure. Thereafter, the resulting residue was separated and purified by a silica gel column chromatography to obtain 330 mg of the title compound (1.3 mmol, 45% in yield).

$^1$H-NMR (CDCl$_3$) δ 2.54–2.60 (2 H, m), 2.72 (2 H, dd, J=5.9 Hz, 5.5 Hz), 3.18 (2 H, dd, J=2.7 Hz, 6.3 Hz), 3.64 (2 H, s), 6.05–6.08 (1 H, m), 7.20–7.40 (10 H, m); MW 249.36 (C$_{18}$H$_{19}$N); Mass spectrum EI m/z 249 (M)$^+$

EXAMPLE 58

1-Benzyl-4-methyl-4-phenyl-piperidine hydrochloride

1-Benzyl-4-phenyl-1,2,3,6-tetrahydropyridine (160 mg, 0.64 mmol) was dissolved in anhydrous tetrahydrofuran (2 ml) to which was subsequently added dropwise n-butyl lithium hexane solution (0.64 mmol) at −10 to −20° C. in an atmosphere of argon, followed by 15 minutes of stirring. After cooling the reaction solution to −50 to −60° C., iodomethane (0.13 ml, 2.1 mmol) was added dropwise thereto and then the solution was stirred for 2 hours while gradually increasing the temperature to −20° C. After adding saturated brine to the reaction solution, the reaction product was extracted with ethyl acetate, and the resulting extract was washed with water and saturated brine and dried with anhydrous sodium sulfate. Then the solvent was evaporated under a reduced pressure. The thus obtained residue was dissolved in methanol (2 ml), and the solution was mixed with palladium-carbon (40 mg) and stirred at room temperature for 38 hours in an atmosphere of hydrogen. The reaction solution was filtered, the resulting mother liquor was mixed with hydrochloric acid-saturated methanol and then the solvent was evaporated under a reduced pressure to obtain crystals which were then washed with a small amount of ethyl acetate to obtain 83 mg of the title compound (0.28 mmol, 43% in yield).

$^1$H-NMR (CDCl$_3$) δ 1.21 (3 H, s), 1.72–1.83 (2 H, m), 2.08–2.19 (2 H, m), 2.36–2.56 (4 H, m), 3.46 (2 H, s), 7.20–7.40 (10 H, m); MW 265.40 (C$_{19}$H$_{23}$N); Mass spectrum FAB m/z 266 (M+H)$^+$

EXAMPLE 59

2a-[4-(4-Methyl-4-phenyl-piperidyl)butyl]-2a,3,4,5-tetrahydrobenz[cd]indole-2(1H)-one 1-Benzyl-4-methyl-4-phenylpiperidine (62 mg, 0.24 mmol) was dissolved in ethanol (2 ml). Thereto was added palladium-carbon (10 mg), and the resulting solution was stirred at a room temperature for 17 hours in an atmosphere of argon. The reaction solution was filtered, the solvent was evaporated from the resulting mother liquor under a reduced pressure, and the thus obtained material was dissolved in anhydrous N,N-dimethylformamide (2 ml). The resulting solution was mixed with 2a-(4-bromobutyl)-2a,3,4,5-tetrahydrobenz[cd]indole-2(1H)-one (79 mg, 0.26 mmol) and potassium carbonate (51mg, 0.37mmol) and then the mixture was stirred at 60° C. for 3 hours. The reaction solution was mixed with ethyl acetate and water, and the reaction product was extracted with ethyl acetate, washed with saturated brine and dried with anhydrous sodium sulfate. Then the compound obtained by the evaporation of the solvent under a reduced pressure was separated and purified by a silica gel column chromatography to obtain 50 mg of the title compound (0.12 mmol, 53% in yield).

$^1$H-NMR (CDCl$_3$) δ 1.00–1.40 (6 H, m), 1.43–1.60 (1 H, m), 1.70–1.95 (6 H, m), 2.00–2.70 (2 H, m), 2.75–2.89 (2 H, m), 6.65 (1 H, d, J=7.8 Hz), 6.79 (1 H, d, J=7.8 Hz), 7.11 (1 H, dd), 7.17–7.35 (5 H, m), 7.41 (1 H, br s); MW 402.58 (C$_{27}$H$_{34}$N$_2$O); Mass spectrum TS m/z 403 (M+H)$^+$ The thus obtained free compound was dissolved in hydrochloric acid-saturated methanol to obtain its hydrochloric acid salt.

MW (C$_{28}$H$_{35}$ClN$_2$O) 439.04; Mass spectrum EI m/z 402 (M–HCl)$^+$

EXAMPLE 60

1-Methylbenz[cd]indole-2(1H)-one

Benz[cd]indole-2(1H)-one (5.1 g, 30 mmol) was dissolved in anhydrous N,N-dimethylformamide (100 ml). Thereto was added sodium hydride (60% content, 1.2 g, 30 mmol), and the resulting solution was stirred for 20 minutes in an ice bath. The reaction solution was mixed with methyl iodide (2.6 ml, 42 mmol) and again stirred at a room temperature for 1 hour. The reaction solution was mixed with ethyl acetate (300 ml) and water (200 ml), and the reaction product was extracted with ethyl acetate. The ethyl acetate layer was separated, washed with water and then dried with anhydrous sodium sulfate. By evaporating ethyl acetate under a reduced pressure, 4.7 g (26 mmol, 74% in yield) of the title compound was obtained as yellow crystals.

MW 183.21 ($C_{12}H_9NO$); Mass spectrum EI m/z 183 (M)$^+$

EXAMPLE 61

1-Methyl-2a,3,4,5-tetrahydrobenz[cd]indole-2(1H)-one

Ethanol and Raney nickel slurry (Aldrich) were added to 1-methyl-benz[cd]indole-2(1H)-one (4.5 g, 25 mmol) to carry out catalytic reduction under ordinary pressure. The reaction was terminated when 1.15 L of hydrogen absorption was observed, Raney nickel was removed by filtration, the resulting filtrate was concentrated and then the thus obtained colorless oil was purified by a silica gel column chromatography to obtain 3.8 g of the title compound (20 mmol, 80% in yield).

$^1$H-NMR (CDCl$_3$) δ 1.31 (1 H, m), 1.91 (1 H, m), 2.14 (1 H, m), 2.42 (1 H, m), 2.64 (1 H, m), 2.92 (1 H, dd), 3.17 (3 H, s), 3.28 (1 H, dd), 6.61 (1 H, d), 6.82 (1 H, d), 7.17 (1 H, t); MW 187.24 ($C_{12}H_{13}NO$); Mass spectrum EI m/z 187 (M)$^+$

EXAMPLE 62

2a-(4-Bromobutyl)-1-methyl-2a,3,4,5-tetrahydrobenz[cd]indole-2(1H)-one

1-Methyl-2a,3,4,5-tetrahydrobenz[cd]indole-2(1H) -one (3.7 g, 20 mmol) was dissolved in anhydrous N,N-dimethylformamide (50 ml). Thereto was added sodium hydride (60% content, 800 mg, 20 mmol), and the resulting solution was stirred at a room temperature for 30 minutes. The reaction solution was cooled in an ice bath of −10° C., mixed with 1,4-dibromobutane (7.0 ml) and then 1 hour of the reaction was carried out while temperature of the reaction solution was increased to a room temperature. The reaction solution was mixed with diisopropyl ether (150 ml) and water (100 ml), and the reaction product was extracted. Then the resulting organic layer was washed three times with water and dried with anhydrous sodium sulfate. Diisopropyl ether was evaporated under a reduced pressure, and the thus obtained oily residue was separated and purified by a silica gel column chromatography (developing system: diisopropyl ether) to obtain 4.8 g of the title compound (15 mmol, 75% in yield).

$^1$H-NMR (CDCl$_3$) δ 1.15 (1 H, m), 1.30 (2 H, m), 1.66–1.92 (5 H, m), 2.00–2.20 (2 H, m), 2.66 (1 H, m), 2.86 (1 H, m), 3.17 (3 H, s), 3.29 (2 H, t), 6.64 (1 H, d), 6.83 (1 H, d), 7.17 (1 H, t); MW 322.25 ($C_{16}H_{20}NOBr$); Mass spectrum EI m/z 321:323 (intensity ratio 1:1 (M)$^+$

EXAMPLE 63

2a-[4-(4-Hydroxy-4-phenylpiperidyl)butyl]-1-methyl-2a,3,4,5-tetrahydrobenz[cd]indole-2(1H)-one A mixture of 2a-(4-bromobutyl)-1-methyl-2a,3,4,5-tetrahydrobenz[cd]indole-2(1H)-one (322 mg, 1 mmol), 4-hydroxy-4-phenylpiperidine (210 mg, 1.2 mmol), sodium bicarbonate (102 mg, 1.2 mmol) and ethanol (15 ml) was heated under reflux for 6.3 hours on an oil bath, the reaction solution was cooled, and the thus precipitated crystals were collected by filtration to obtain 226 mg of the title compound (0.54 mmol, 54% in yield).

$^1$H-NMR (CDCl$_3$) δ 0.93–1.05 (1 H, m), 1.12–1.49 (4 H, m), 1.67–1.92 (5 H, m), 2.06–2.20 (4 H, m), 2.22–2.41 (4 H, m), 2.60–2.77 (4 H, m), 2.81–2.91 (1 H, m), 3.17 (3 H, s), 6.64 (1 H, d, J=7.8 Hz), 6.82 (1 H, d, J=7.6 Hz), 7.18 (1 H, dd), 7.25 (1 H, t, J=7.3 Hz), 7.34 (2 H, dd, J=8.0 Hz), 7.50 2 H, d); MW 418.58 ($C_{27}H_{34}N_2O_2$); Mass spectrum EI m/z 418 (M)$^+$

EXAMPLE 64

2a-[4-(4-Methoxy-4-phenyl-piperidyl)butyl]-1-methyl-2a,3,4,5-tetrahydrobenz[cd]indole-2(1H)-one 1-t-Butoxycarbonyl-4-methoxy-4-phenyl-piperidine (510 mg, 1.7 mmol) was dissolved in dichloromethane (2 ml). Thereto was added trifluoroacetic acid (4 ml), and the resulting solution was stirred at a room temperature for 30 minutes. The reaction solution was diluted with ethyl acetate, washed with sodium hydroxide aqueous solution (1 N) and dried with anhydrous sodium sulfate. The solvent was evaporated under a reduced pressure, and the thus obtained material was dissolved in anhydrous N,N-dimethylformamide (2 ml). Then the resulting solution was mixed with 1-methyl-2a-(4-bromobutyl)-2a,3,4,5-tetrahydrobenz[cd]indole-2(1H) -one (450 mg, 1.4 mmol) and potassium carbonate (290 mg, 2.1 mmol) and stirred at 60° C. for 3 hours. The reaction solution was mixed with ethyl acetate and water, and the reaction product was extracted with ethyl acetate, washed with saturated brine and dried with anhydrous sodium sulfate. Then the compound obtained by the evaporation of the solvent under a reduced pressure was separated and purified by a silica gel column chromatography to obtain 79 mg of the title compound (0.31 mmol, 18% in yield).

$^1$H-NMR (CDCl$_3$) δ 0.93–1.06 (1 H, m), 1.13–1.34 (2 H, m), 1.40–1.51 (1 H, m), 1.72–1.93 (4 H, m), 1.96–2.20 (6 H, m), 2.28–2.47 (4 H, m), 2.60–2.81 (3 H, m), 2.81–2.92 (1 H, m), 2.95 (3 H, s), 3.17 (3 H, s), 6.63 (1 H, d, J=7.6 Hz), 6.82 (1 H, d, J=8.0 Hz), 7.18 (1 H, dd), 7.24–7.39 (5 H, m); MW 432.59 ($C_{28}H_{36}N_2O_2$); Mass spectrum EI m/z 432 (M)$^+$

EXAMPLE 65

2a-[4-(4-Acetyl-4-phenyl-piperidyl)butyl]-2a,3,4,5-tetrahydrobenz[cd]indole-2(1H)-one 2a-(3-Formylpropyl)-2a,3,4,5-tetrahydrobenz[cd]indole-2(1H)-one (180 mg, 0.72 mmol), 4-acetyl-4-phenylpiperidine hydrochloride (190 mg, 0.79 mmol), acetic acid (430 mg, 7.2 mmol) and sodium triacetoxyborate (310 mg, 1.4 mmol) were stirred in 1,2-dichloroethane (3 ml) at a room temperature for 20 hours. The reaction solution was mixed with ethyl acetate (80 ml), washed with sodium hydroxide aqueous solution (1 N) and saturated brine and dried with anhydrous sodium sulfate. Then the compound obtained by the evaporation of the solvent under a reduced pressure was separated and purified by a silica gel column chromatography to obtain 74 mg of the title compound (0.17 mmol, 24% in yield).

$^1$H-NMR (CDCl$_3$) δ 0.98–1.11 (1 H, m), 1.22–1.45 (5 H, m), 1.72–1.93 (7 H, m), 1.98–2.27 (6 H, m), 2.37–2.49 (2 H, m), 2.58–2.71 (3 H, m), 2.77–2.87 (1 H, m), 6.66 (1 H. d, J=7.6 Hz), 6.79 (1 H, d, J=7.8 Hz), 7.10 (1 H, dd), 7.22–7.36 (5 H, m), 7.48 (1 H, br s); MW 430.59 ($C_{28}H_{34}N_2O_2$); Mass spectrum EI m/z 430 (M)$^+$

EXAMPLE 66

6-Acetyl-2a,3,4,5-tetrahydrobenz[cd]indole-2(1H)-one

A 3.1 ml (43.4 mmol) portion of acetyl chloride was added to a carbon disulfide suspension (100 ml) of aluminum chloride (11.5 g, 86.7 mmol) and stirred at a room temperature for 30 minutes. Thereto was added dropwise a carbon disulfide solution (150 ml) of 2a,3,4,5-tetrahydrobenz[cd]indole-2(1H)-one (5.0 g, 28.9 mmol) spending 2 hours. After 2 hours of heating under reflux and confirmation of the disappearance of the material by a thin layer chromatography, this was returned to a room temperature and mixed with isopropyl ether. The supernatant fluid was discarded by decantation, and the remaining rubber-like substance was dissolved in ethyl acetate and washed with water. The water layer was extracted with ethyl acetate, the organic layers were combined and dried ($Na_2SO_4$), and then the solvent was evaporated under a reduced pressure. By recrystallizing the thus obtained oily substance from ethyl acetate-isopropyl ether and then from methanol-isopropyl ether, 3.5 g of the title compound was obtained (yield, 56%).

$^1$H-NMR (CDCl$_3$) δ 1.36 (1 H, m), 1.86 (1 H, m), 2.20 (1 H, m), 2.42 (1 H, m), 2.56 (3 H, s), 2.97 (1 H, m), 3.37 (2 H, m), 6.81 (1 H, d), 7.78 (1 H, d), 9.46 (1 H, s). EI m/z 215 (M)$^+$

The filtrate was concentrated under a reduced pressure and purified by a silica gel column chromatography (300 cc; elution with ethyl acetate-hexane=1:2) to obtain 1.1 g of the title compound (yield, 18%) and 1.0 g of 8-acetyl-2a,3,4,5-tetrahydrobenz[cd]indole-2(1H) -one (yield, 17%).

$^1$H-NMR (CDCl$_3$): δ 1.33 (1 H, m), 1.90 (1 H, m), 2.17 (1 H, m), 2.45 (1 H, m), 2.57 (3 H, s), 2.65 (1 H, m), 2.95 (1 H, dd), 3.27 (2 H, dd), 6.83 (1 H, d), 7.57 (1 H, d), 9.32 (1 H, s). EI m/z 215 (M)$^+$

EXAMPLE 67

6-Acetyl-2a-(4-bromobutyl)-2a,3,4,5-tetrahydrobenz[cd]indole-2(1H)-one

A 170 ml portion of DMF solution of 6-acetyl-2a,3,4,5-tetrahydrobenz[cd]indole-2(1H)-one (3.2 g, 14.9 mmol) was cooled to −5° C. Thereto was added 0.7 g of sodium hydride (16.4 mmol), and the resulting solution was stirred at 0° C. for 30 minutes and then cooled to −40° C. Thereto was added 8.9 ml of 1,4-dibromobutane (74.5 mmol), and the mixture was stirred overnight while gradually increasing the temperature in an atmosphere of argon. The reaction solution was extracted with ethyl acetate and washed with water. After drying ($Na_2SO_4$), the oily substance obtained by the evaporation of the solvent under a reduced pressure was purified by a silica gel column chromatography (700 cc; elution with ethyl acetate-hexane=2:3) and then recrystallized from ethyl acetate-hexane to obtain 2.26 g of the title compound (43% in yield).

$^1$H-NMR (CDCl$_3$) δ 1.43 (2 H, m), 1.72–1.91 (4 H, m), 2.12 (2 H, m), 2.57 (3 H, s), 3.11 (1 H, m), 3.23 (1 H, m), 3.30 (2 H, t), 6.79 (1 H, d), 7.76 (1 H, d), 8.37 (1 H, s).

EXAMPLE 68

6-Acetyl-2a-[4-(2-methoxyphenylpiperazinyl)butyl]-2a,3,4,5-tetrahydrobenz[cd]indole-2(1H)-one To 7 ml of DMF solution of 6-acetyl-2a-(4-bromobutyl)-2a,3,4,5-tetrahydrobenz[cd]indole-2(1H) -one (0.27 g, 0.77 mmol) were added 0.22 g (1.16 mmol) of 2-methoxyphenylpiperazine and 0.32 g (2.31 mmol) of potassium carbonate, subsequently stirring overnight at a room temperature. The reaction solution was extracted with ethyl acetate and washed with water. After drying ($Na_2SO_4$), the solvent was evaporated under a reduced pressure, and the thus obtained oily substance was purified by a silica gel column chromatography (80 cc; elution with chloroform-methanol=40:1) to obtain 0.28 g of the title compound (79% in yield).

$^1$H-NMR (CDCl$_3$) δ 1.06 (1 H, m), 1.24–1.48 (4 H, m), 1.85 (3 H, m), 2.10 (2 H, m), 2.32 (2 H, m), 2.56 (3 H, s), 2.58 (4 H, m), 3.05–3.14 (5 H, m), 3.24 (1 H, m), 3.84 (3 H, s), 6.74 (1 H, d), 6.83–7.00 (4 H, m), 7.73 (1 H, d), 8.77 (1 H, s). LC m/z 462 (M+H)$^+$

EXAMPLE 69

6-Acetyl-2a-[4-(1,2,3,6-tetrahydro-4-phenylpyridinyl)butyl]-2a,3,4,5-tetrahydrobenz[cd]indole-2(1H)-one In the same manner as described in Example (68), 57.6 mg (yield, 24%) of the title compound was obtained from 0.20 g (0.57 mmol) of 6-acetyl-2a-(4-bromobutyl)-2a,3,4,5-tetrahydrobenz[cd]indole-2(1H)-one and 168 mg (0.86 mmol) of 1,2,3,6-tetrahydro-4-phenylpyridine.

$^1$H-NMR (CDCl$_3$): δ 1.09 (1 H, m), 1.29–1.52 (4 H, m), 1.85 (3 H, m), 2.12 (2 H, m), 2.36 (2 H, m), 2.54 (2 H, m), 2.55 (3 H, s), 2.64 (2 H, m), 3.11 (3 H, m), 3.23 (1 H, m), 6.01 (1 H, m), 6.75 (1 H, d), 7.19–7.36 (5 H, m), 7.72 (1 H, d), 8.73 (1 H, s). LC m/z 429 (M+H)$^+$

EXAMPLE 70

6-Acetoxy-2a-(4-bromobutyl)-2a,3,4,5-tetrahydrobenz[cd]indole-2(1H)-one

A 2 ml portion of methylene chloride solution of 2a-(4-bromobutyl)-2a,3,4,5-tetrahydrobenz[cd]indole-2(1H)-one (94 mg, 0.26 mmol) was cooled to 0° C. and then mixed with 93 mg (0.52 mmol) of m-chloroperbenzoic acid and 21 μl (0.26 mmol) of trifluoroacetic acid. After 2 hours of stirring in the dark at a room temperature, the reaction solution was extracted with chloroform and washed with sodium sulfite and sodium bicarbonate in that order. After drying ($Na_2SO_4$), the solvent was evaporated under a reduced pressure, and the thus obtained oily substance was purified by a silica gel column chromatography (20 cc; elution with ethyl acetate-hexane=1:2) to obtain 88 mg of the title compound (89% in yield).

$^1$H-NMR (CDCl$_3$) δ 1.27–1.52 (3 H, m), 1.71–1.90 (5 H, m), 2.12 (2 H, m), 2.30 (3 H, s), 2.59 (2 H, m), 3.32 (2 H, t), 6.71 (1 H, d), 6.84 (1 H, d), 8.72 (1 H, s)

EXAMPLE 71

6-Acetoxy-2a-[4-(2-methoxyphenylpiperazinyl)butyl]-2a,3,4,5-tetrahydrobenz[cd]indole-2(1H)-one A 2 ml portion of DMF solution of 300 mg (0.82 mmol) 6-acetoxy-2a-(4-bromobutyl)-2a,3,4,5-tetrahydrobenz[cd]indole-2(1H)-one (1.0 g, 5.8 mmol) was mixed with 315 mg (1.64 mmol) of 2-methoxyphenylpiperazine and 0.57 ml (3.28 mmol) of N,N-diisopropylethylamine, and the mixture was stirred overnight at a room temperature. The reaction solution was extracted with ethyl acetate and washed with water. After drying ($Na_2SO_4$), the solvent was evaporated under a reduced pressure, and the thus obtained oily substance was purified by a silica gel column chromatography (80 cc; elution with chloroform-methanol=30:1) to obtain 143 mg of the title compound (36% in yield).

$^1$H-NMR (CDCl$_3$): δ 1.16 (1 H, m), 1.36 (3 H, m), 1.44 (2 H, m), 1.73–1.90 (4 H, m), 2.30 (3 H, s), 2.33 (2 H, m), 2.59 (4 H, m), 3.06 (4 H, m), 3.85 (3 H, s), 6.67 (1 H, d), 6.83–7.00 (5 H, m), 8.66 (1 H, s). LC m/z 462 (M+H)

EXAMPLE 72

6-Hydroxy-2a-[4-(2-methoxyphenylpiperazinyl) butyl]-2a,3,4.5-tetrahydrobenz[cd]indole-2(1H)-one A methanol solution of 121 mg (0.25 mmol) of 6-acetoxy-2a-[4-(2-methoxyphenylpiperazinyl)butyl]-2a,3,4,5-tetrahydrobenz[cd]indole-2(1H) -one was mixed with 30 mg of methanol solution of sodium methoxide and the mixture was stirred at a room temperature for 3 hours. By evaporating the solvent under a reduced pressure and recrystallizing the resulting residue from chloroform-ethyl acetate, the title compound was obtained quantitatively.

$^1$H-NMR (CDCl$_3$): δ 1.15 (1 H, m), 1.34 (2 H, m), 1.59 (3 H, m), 1.76–1.85 (4 H, m), 2.09 (2 H, m), 2.49 (2 H, m), 2.67–2.78 (4 H, m), 3.20 (4 H, m), 3.85 (3 H, s), 6.54 (1 H, d), 6.60 (1 H. d), 6.85–7.03 (4 H, m), 7.18 (1 H, s). LC m/z 436 (M+H)$^+$

EXAMPLE 73

6-Acetoxy-2a-[4-(1,2,3,6-tetrahydro-4-phenylpyridinyl)butyl]-2a,3,4,5-tetrahydrobenz[cd] indole-2(1H)-one In the same manner as described in Example (71), 64 mg (yield, 38%) of the title compound was obtained from 0.14 g (0.38 mmol) of 6-acetoxy-2a-(4-bromobutyl)-2a,3,4,5-tetrahydrobenz[cd]indole-2(1H)-one and 0.15 g (0.76 mmol) of 1,2,3,6-tetrahydro-4-phenylpyridine.

$^1$H-NMR (CDCl$_3$): δ 1.16 (1 H, m), 1.34 (2 H, m)r, 1.48 (3 H, m), 1.84 (3 H, m), 2.09 (2 H, m), 2.29 (3 H, s), 2.38 (2 H, m), 2.57 (4 H, m), 2.64 (2 H, m), 3.10 (2 H, m), 6.02 (1 H. m), 6.68 (1 H, d), 7.19–7.37 (5 H, m), 8.61 (1 H, s). LC m/z 445 (M+H)$^+$

EXAMPLE 74

6-Hydroxy-2a-[4-(1,2,3,6-tetrahydro-4-phenylpyridinyl)butyl]-2a,3,4,5-tetrahydrobenz[cd] indole-2(1H)-one In the same manner as described in Example (72), the title compound was obtained from 6-acetoxy-2a-[4-(1,2,3,6-tetrahydro-4-phenylpyridinyl)butyl]-2a,3,4,5-tetrahydrobenz[cd]indole-2(1H)-one.

$^1$H-NMR (CDCl$_3$): δ 1.11 (1 H, m), 1.30 (2 H, m), 1.47 (2 H, m), 1.82 (3 H, m), 2.08 (2 H, m), 2.37 (2 H, m), 2.55–2.69 (5 H, m), 2.77 (2 H, m), 3.11 (2 H, m), 6.04 (1 H, m), 6.53 (1 H, d), 6.59 (1 H, d), 7.19–7.38 (5 H, m), 7.98 (1 H, s). LC m/z 403 (M+H)$^+$

EXAMPLE 75

6-Methoxy-2a-(4-bromobutyl)-2a,3,4,5-tetrahydrobenz[cd]indole-2(1H)-one

A 16 ml portion of methanol solution of 6-acetoxy-2a-(4-bromobutyl)-2a,3,4,5-tetrahydrobenz[cd]indole-2(1H)-one (0.60 g, 1.64 mmol) was mixed with sodium methoxide and stirred at a room temperature for 3 hours. After neutralization of the reaction solution with an ion exchange resin Amberlite 15, the resin was removed by filtration and the solvent was evaporated under a reduced pressure. The thus obtained oily substance was dissolved in 4 ml of acetone, and the solution was mixed with 2 ml of methyl iodide and 2 ml of potassium carbonate aqueous solution and stirred overnight at room temperature. The reaction solution was extracted with ethyl acetate and washed with 1 N hydrochloric acid. After drying (Na$_2$SO$_4$), the solvent was evaporated under a reduced pressure, and the thus obtained oily substance was purified by a silica gel column chromatography (100 cc; elution with ethyl acetate-hexane=1:2) to obtain 0.31 g of the title compound (56% in yield).

$^1$H-NMR (CDCl$_3$): δ 1.18–1.48 (3 H, m), 1.70–1.93 (5 H, m), 2.09 (2 H, m), 2.61 (1 H, m), 2.78 (1 H, m), 3.07 (2 H, t), 3.79 (3 H, s), 6.61 (1 H, d), 6.65 (1 H, d), 8.22 (1 H, s).

EXAMPLE 76

6-Methoxy-2a-[4-(2-methoxyphenylpiperazinyl) butyl]-2a,3,4,5-tetrahydrobenz[cd]indole-2(1H)-one In the same manner as described in Example (68), 159 mg (yield, 88%) of the title compound was obtained from 135 mg (0.40 mmol) of 6-methoxy-2a-(4-bromobutyl)-2a,3,4,5-tetrahydrobenz[cd]indole-2(1H)-one and 153 mg (0.80 mmol) of 2-methoxyphenylpiperazine.

$^1$H-NMR (CDCl$_3$): δ 1.12 (1 H, m), 1.25–1.48 (5 H, m), 1.73–1.89 (3 H, m), 2.09 (2 H, m), 2.30 (2 H, m), 2.61 (5 H, m), 2.78 (1 H, m), 3.05 (3 H, m), 3.77 (3 H, s), 3.83 (3 H, s), 6.58 (1 H, d), 6.62 (1 H, d), 6.82–6.99 (4 H, m), 8.87 (1 H, s). LC m/z 450 (M+H)$^+$

EXAMPLE 77

6-Methoxy-2a-[4-(1,2,3,6-tetrahydro-4-phenylpyridinyl)butyl]-2a,3,4,5-tetrahydrobenz[cd] indole-2(1H)-one In the same manner as described in Example (68), 83 mg (yield, 50%) of the title compound was obtained from 135 mg (0.40 mmol) of 6-methoxy-2a-(4-bromobutyl)-2a,3,4,5-tetrahydrobenz[cd]indole-2(1H)-one and 156 mg (0.80 mmol) of 1,2,3,6-tetrahydro-4-phenylpyridine.

$^1$H-NMR (CDCl$_3$): δ 1.14 (1 H, m), 1.34 (2 H, m), 1.47 (2 H, m), 1.75–1.90 (3 H, m), 2.10 (2 H, m), 2.35 (2 H, m), 2.52–2.64 (5 H, m), 2.77 (1 H, m), 3.08 (2 H, m), 3.79 (3 H, s), 6.01 (1 H, m), 6.59 (1 H, d), 6.63 (1 H, d), 7.19–7.37 (5 H, m), 8.07 (1 H, s). LC m/z 417 (M+H)$^+$

EXAMPLE 78

6-Methoxycarbonyl-2a-(4-bromobutyl)-2a,3,4,5-tetrahydrobenz[cd]-indole-2(1H)-one A 1.44 g (4.87 mmol) portion of triphosgene was added to 1,2-dichloroethane suspension (30 ml) of aluminum chloride (1.95 g, 14.61 mmol) and the mixture was cooled to 0° C. Thereto was added 30 ml of 1,2-dichloroethane solution containing 1.50 g (1.64 mmol) of 2a-(4-bromobutyl)-2a,3,4,5-tetrahydrobenz[cd]indole-2(1H)-one, subsequently carrying out 2 hours of stirring at 0° C. The reaction solution was mixed with 50 ml of methanol, stirred at a room temperature for 1 hour, extracted with chloroform and then washed with 1 N hydrochloric acid. After drying (Na$_2$SO$_4$), the solvent was evaporated under a reduced pressure, and the thus obtained oily substance was purified by a silica gel column chromatography (300 cc; elution with ethyl acetate-hexane=1:1) and then recrystallized from ethyl acetate-hexane to obtain 0.63 g of the title compound (35% in yield).

$^1$H-NMR (CDCl$_3$) δ 1.23 (1 H, m), 1.41 (1 H, m), 1.71–1.92 (5 H, m), 2.14 (2 H, m), 3.08 (1 H, m), 3.30 (3 H, m), 3.87 (3 H, s), 6.81 (1 H, d), 7.94 (1 H, d), 8.76 (1 H, s).

EXAMPLE 79

6-Methoxycarbonyl-2a-[4-(2-methoxyphenylpiperazinyl)butyl]-2a,3,4,5-tetrahydrobenz[cd]indole-2(1H)-one In the same manner as described in Example (68), 311 mg (yield, 79%) of the title compound was obtained from 300 mg (0.82 mmol) of 6-methoxycarbonyl-2a-(4-bromobutyl)-2a,3,4,5-tetrahydrobenz[cd]indole-2(1H)-one and 315 mg (1.64 mmol) of 2-methoxyphenylpiperazine.

$^1$H-NMR (CDCl$_3$): δ 1.06 (1 H, m), 1.34 (3 H, m), 1.50 (2 H, m), 1.86 (4 H, m), 2.11 (2 H, m), 2.41 (2 H, m), 2.71 (3 H, m), 3.07 (4 H, m), 3.29 (1 H, m), 3.84 (3 H, s), 3.86 (3 H, s), 6.74 (1 H, d), 6.83–7.01 (4 H, m), 7.91 (1 H, d), 9.20 (1 H, s). LC m/z 478 (M+H)$^+$

EXAMPLE 80

6-Methoxycarbonyl-2a-[4-(1,2,3,6-tetrahydro-4-phenylpyridinyl)-butyl]-2a,3,4,5-tetrahydrobenz[cd]indole-2(1H)-one In the same manner as described in Example (68), 267 mg (yield, 81%) of the title compound was obtained from 270 mg (0.74 mmol) of 6-methoxycarbonyl-2a-(4-bromobutyl)-2a,3,4,5-tetrahydrobenz[cd]indole-2(1H)-one and 288 mg (1.48 mmol) of 1,2,3,6-tetrahydro-4-phenylpyridine.

$^1$H-NMR (CDCl$_3$): δ 1.07 (1 H, m), 1.30–1.49 (4 H, m), 1.85 (3 H, m), 2.12 (2 H, m), 2.35 (2 H, m), 2.52 (2 H, m), 2.63 (2 H, t), 3.08 (3 H, m), 3.28 (1 H, m), 3.85 (3 H, s), 6.01 (1 H, m), 6.74 (1 H, d), 7.18–7.35 (5 H, m), 7.91 (1 H, d), 9.32 (1 H, s). LC m/z 445 (M+H)$^+$

EXAMPLE 81

6-Carbamoyl-2a-[4-(2-methoxyphenylpiperazinyl)butyl]-2a,3,4,5-tetrahydrobenz[cd]indole-2(1H)-one A methanol solution (3 ml) containing 100 mg (0.21 mmol) of 6-methoxycarbonyl-2a-[4-(2-methoxyphenylpiperazinyl)butyl]-2a,3,4,5-tetrahydrobenz[cd]indole-2(1H)-one was mixed with 10% lithium hydroxide aqueous solution (1 ml) and heated under reflux for 30 hours. The reaction solution was returned to a room temperature and acidified by adding 5 N hydrochloric acid. The thus formed insoluble matter was filtered, washed with water and then dried under a reduced pressure to obtain 92 mg (94% in yield) of a carboxylic acid derivative. A 30 mg (0.06 mmol) portion of the thus obtained carboxylic acid derivative was dissolved in DMF (1 ml), and the solution was mixed with 20 mg (0.10 mmol) of dicyclohexylcarbodiimide (DCC) and 13mg (0.10 mmol) of 1-hydroxybenzotriazole (HOBt). The thus obtained solution was stirred at a room temperature for 3 hours, cooled to 0° C., mixed with 1 ml of 28% aqueous ammonia and then again stirred at a room temperature for 2 hours. The solvent was evaporated under a reduced pressure, and the thus obtained residue was allowed to be adsorbed by Diaion HP-20 (Mitsubishi Kagaku). Thereafter, 26 mg (86% in yield) of the title compound was obtained by its elution with water-methanol=10:1 (300 ml), the same=1:1 (200 ml) and methanol (300 ml) in that order.

$^1$H-NMR (CD$_3$OD): δ 0.91 (1 H, m), 1.19 (3 H, m), 1.34 (2 H, m), 1.67–1.84 (3 H, m), 1.96 (1 H, m), 2.06 (1 H, m), 2.23 (2 H, m), 2.50 (4 H, br s), 2.92 (5 H, m), 3.73 (3 H, s), 6.66 (1 H, d), 6.76–6.91 (4 H, m), 7.36 (1 H, d). LC m/z 463 (M+H)$^+$

EXAMPLE 82

6-Carbamoyl-2a-[4-(1,2,3,6-tetrahydro-4-phenylpyridinyl)butyl]-2a,3,4,5-tetrahydrobenz[cd]indole-2(1H)-one In the same manner as described in Example 81, the title compound (yield, 48%) was obtained from 6-methoxycarbonyl-2a-(4-(1,2,3,6-tetrahydro-4-phenylpyridinyl)butyl]-2a,3,4,5-tetrahydrobenz[cd]indole-2(1H)-one.

$^1$H-NMR (CD$_3$OD): δ 1.03 (1 H, m), 1.33 (2 H, m), 1.64 (1 H, m), 1.72 (1 H, m), 1.86 (2 H, m), 2.07 (1 H, m), 2.20 (1 H, m), 2.37 (2 H, m), 2.56 (2 H, m), 2.69 (2 H, t), 2.95–3.11 (3 H, m), 3.45 (1 H, m), 6.07 (1 H, m), 6.76 (1 H, d), 7.19–7.40 (5 H, m), 7.46 (1 H, d). LC m/z 430 (M+H)$^+$

EXAMPLE 83

6-Bromo-2a-(4-bromobutyl)-2a,3,4,5-tetrahydrobenz[cd]indole-2(1H)-one

A 20 ml portion of 1,2-dichloroethane solution containing 0.50 g (1.62 mmol) of 2a-(4-bromobutyl)-2a,3,4,5-tetrahydrobenz[cd]-indole-2(1H)-one was cooled to −20° C. and mixed with 0.10 ml (1.94 mmol) of bromine. The reaction solution was stirred at −20° C. for 1 hour, extracted with chloroform and then washed with saturated sodium thiosulfate aqueous solution and saturated sodium bicarbonate aqueous solution in that order. After drying (Na$_2$SO$_4$), the solvent was evaporated under a reduced pressure, and the thus obtained residue was re-precipitated from ethyl acetate-hexane to obtain 0.54 g of the title compound (86% in yield).

$^1$H-NMR (CDCl$_3$) δ 1.19–1.52 (3 H, m), 1.70–2.00 (5 H, m), 2.14 (2 H, m), 2.74 (2 H, t), 3.31 (2 H, t), 6.64 (1 H, d), 7.34 (1 H, d), 8.61 (1 H, s).

EXAMPLE 84

6-Bromo-2a-[4-(2-methoxyphenylpiperazinyl)butyl]-2a,3,4,5-tetrahydrobenz[cd]indole-2(1H)-one In the same manner as described in Example 68, 246 mg (yield, 87%) of the title compound was obtained from 220 mg (0.57 mmol) of 6-bromo-2a-(4-bromobutyl)-2a,3,4,5-tetrahydrobenz[cd]indole-2(1H)-one and 219 mg (1.14 mmol) of 2-methoxyphenylpiperazine.

$^1$H-NMR (CDCl$_3$): δ 1.08 (1 H, m), 1.26–1.46 (4 H, m), 1.72–1.96 (3 H, m), 2.14 (2 H, m), 2.31 (2 H, m), 2.59 (4 H, br s), 2.73 (2 H, t), 3.06 (4 H, br s), 3.84 (3 H, s), 6.57 (1 H, d), 6.83–7.00 (4 H, m), 7.31 (1 H, d), 9.04 (1 H, s). LC-MS m/z 498, 500 (1:1) (M+H)$^+$

EXAMPLE 85

6-Bromo-2a-[4-(1,2,3,6-tetrahydro-4-phenylpyridinyl)butyl]-2a,3,4,5-tetrahydrobenz[cd]indole-2(1H)-one In the same manner as described in Example 68, 194 mg (yield, 73%) of the title compound was obtained from 220 mg (0.57 mmol) of 6-bromo-2a-(4-bromobutyl)-2a,3,4,5-tetrahydrobenz[cd]indole-2(1H)-one and 222 mg (1.14 mmol) of 1,2,3,6-tetrahydro-4-phenylpyridine.

$^1$H-NMR (CDCl$_3$): δ 1.11 (1 H, m), 1.31 (2 H, m), 1.46 (2 H, m), 1.72–1.93 (3 H, m), 2.13 (2 H, m), 2.35 (2 H, m), 2.52 (2 H, m), 2.63 (2 H, t), 2.72 (2 H, t), 3.08 (2 H, m), 6.01 (1 H, m), 6.59 (1 H, d), 7.19–7.31 (6 H, m), 9.16 (1 H, s). LC m/z 465, 467 (1:1) (M+H)$^+$

EXAMPLE 86

6-Nitro-2a-(4-bromobutyl)-2a,3,4,5-tetrahydrobenz[cd]indole-2(1H)-one

A 100 mg (0.32 mmol) portion of 2a-(4-bromobutyl)-2a,3,4,5-Tetrahydrobenz[cd]indole-2(1H)-one was dissolved in 2 ml of acetic acid, and the resulting solution was cooled to 15° C. Thereto was added acetic acid solution (1 ml) containing 46 al (0.48 mmol) of acetic anhydride and 19 μl (0.48 mmol) of nitric acid, and the mixture was stirred overnight at 15° C. The reaction solution was extracted with chloroform and washed with water and sodium bicarbonate aqueous solution in that order. After drying ($Na_2SO_4$), the solvent was evaporated under a reduced pressure, and the resulting residue was purified by a silica gel column chromatography (20 cc; elution with ethyl acetate-hexane=1:2) to obtain 83 mg of the title compound (73% in yield). 1H-NMR ($CDCl_3$): δ 1.25 (1 H, m), 1.46 (2 H, m), 1.73–2.02 (5 H, m), 2.18 (2 H, m), 3.24 (2 H, m), 3.33 (2 H, t), 6.89 (1 H, d), 8.15 (1 H, d), 9.07 (1 H, s). EI m/z 352, 354 (1:1) $(M+H)^+$

EXAMPLE 87

2a-[4-{4-($^2$-Pyridyl)piperazinyl}butyl]-2a,3,4,5-tetrahydrobenz[cd]indole-2(1H)-one 2a-(4-Bromobutyl)-2a,3,4,5-tetrahydrobenz[cd]indole-2(1H)-one (147 mg, 0.48 mmol), 1-(2-pyridyl)piperazine (86 mg, 0.53 mmol) and potassium carbonate (99 mg, 0.72 mmol) were stirred overnight in anhydrous N,N-dimethylformamide (2 ml) at 60° C. The solvent was evaporated under a reduced pressure, and the thus obtained residue was mixed with ethyl acetate and water. The reaction product was extracted with ethyl acetate, washed with saturated brine and dried with anhydrous sodium sulfate, the solvent was evaporated under a reduced pressure and then the thus obtained substance was separated and purified by a silica gel column chromatography to obtain 190 mg of the title compound (0.48 mmol, 100% in yield).

$^1$H-NMR ($CDCl_3$) δ 1.03–1.52 (5 H, m), 1.75–1.92 (5 H, m), 2.06–2.19 (2 H, m), 2.22–2.34 (2 H, m), 2.60–2.69 (1 H, m), 2.79–2.89 (1 H, m), 3.47–3.52 (4 H, m), 6.59–6.63 (2 H, s), 6.67 (1 H, d, J=7.4 Hz), 6.80 (1 H, d, J=7.8 Hz), 7.17 (1 H, dd), 7.46 (1 H, d, J=8.0, 7.6, 2.0 Hz), 7.62 (1 H, br s), 8.17 (1 H, m); MW 390.53 ($C_{24}H_{30}N_4O$); Mass spectrum LC m/z 391 $(M+H)^+$ The thus obtained free compound was dissolved in hydrochloric acid-saturated methanol to obtain its hydrochloric acid salt.

MW 426.99 ($C_{24}H_{31}ClN_4O$); Mass spectrum LC m/z 391 $(M-HCl+H)^+$

EXAMPLE 88

2a-[4-{4-(2-Pyrimidyl)piperazinyl}butyl]-2a,3,4,5-tetrahydrobenz[cd]indole-2(1H)-one This compound was synthesized in the same manner as described in Example 87, except that 1-(2-pyrimidyl)piperazine hydrochloride was used in stead of 1-(2-pyridyl)piperazine (yield, 79%).

$^1$H-NMR ($CDCl_3$) δ 1.02–1.14 (1 H, m), 1.26–1.51 (4 H, m), 1.75–1.92 (3 H, m), 2.06–2.18 (2 H, m), 2.22–2.34 (2 H, m), 2.60–2.70 (1 H, m), 2.80–2.90 (1 H, m), 3.77–3.79 (4 H, m), 6.47 (1 H, dd, J=4.7, 1.6 Hz), 6.66 (1 H, d, J=7.8 Hz), 6.80 (1 H, d, J=7.8 Hz), 7.28 (1 H, br s), 8.29 (2 H, dd); MW 391.52 ($C_{23}H_{29}N_5O$); Mass spectrum FAB m/z 392 $(M+H)^+$ The thus obtained free compound was dissolved in hydrochloric acid-saturated methanol to obtain its hydrochloric acid salt.

MW 427.98 ($C_{23}H_{30}ClN_5O$); Mass spectrum LC m/z 391 $(M-HCl)^+$

EXAMPLE 89

2a-[4-{4-(6-(Trifluoromethyl)pyrid-2-yl)piperazinyl}butyl]-2a,3,4,5-tetrahydrobenz[cd]indole-2(1H)-one This compound was synthesized in the same manner as described in Example 87, except that 1-(6-(trifluoromethyl)pyrid-2-yl)piperazine was used in stead of 1-(2-pyridyl)piperazine (yield, 80%).

$^1$H-NMR ($CDCl_3$) δ 1.04–1.17 (1 H, m), 1.29–1.52 (4 H, m), 1.71–1.92 (3 H, m), 2.06–2.20 (2 H, m), 2.22–2.36 (2 H, m), 2.41–2.50 (4 H, m), 2.60–2.70 (1 H, m), 2.80–2.90 (1 H, m), 3.52–3.60 (4 H, m), 6.67 (1 H, d, J=7.6 Hz), 6.74 (1 H, d, J=8.8 Hz), 6.81 (1 H, d, J=7.6 Hz), 6.92 (1 H, d, J=7.6 Hz), 7.12 (1 H, dd), 7.40 (1 H, br s), 7.55 (1 H, dd); MW 458.53 ($C_{25}H_{29}F_3N_4O$); Mass spectrum TSP m/z 459 $(M+H)^+$ The thus obtained free compound was dissolved in hydrochloric acid-saturated methanol to obtain its hydrochloric acid salt.

MW 494.99 ($C_{25}H_{30}ClF_3N_4O$); Mass spectrum TSP m/z 459 $(M-HCl)^+$

EXAMPLE 90

2a-[4-{4-(3-(Trifluoromethyl)pyrid-2-yl)piperazinyl}butyl]-2a,3,4,5-tetrahydrobenz[cd]indole-2 (1H) -one This compound was synthesized in the same manner as described in Example 87, except that 1-(3-(trifluoromethyl)pyrid-2-yl)piperazine was used in stead of 1-(2-pyridyl)piperazine (yield, 81%).

H-NMR ($CDCl_3$) δ 1.03–1.14 (1 H, m), 1.30–1.50 (4 H, m), 1.76–1.92 (3 H, m), 2.06–2.19 (2 H, m), 2.25–2.35 (2 H, m), 2.47–2.54 (4 H, m), 2.60–2.70 (1 H, m), 2.80–2.90 (1 H, m), 3.26–3.34 (4 H, m), 6.67 (1 H, d, J=7.6 Hz), 6.80 (1 H, d, J=8.0 Hz), 6.91–6.95 (1 H, m), 7.11 (1 H, dd), 7.31 (1 H, br s), 7.81–7.83 (1 H, m), 8.39–8.40 (1 H, m); MW 458.53 ($C_{25}H_{29}F_3N_4O$); Mass spectrum TSP m/z 459 $(M+H)^+$ The thus obtained free compound was dissolved in hydrochloric acid-saturated methanol to obtain its hydrochloric acid salt.

MW 494.99 ($C_{25}H_{30}ClF_3N_4O$); Mass spectrum TSP m/z 459 $(M-HCl)^+$

TEST EXAMPLE 1

Binding Affinity for 5-$HT_7$ Receptor

Cultured cells capable of expressing human serotonin 5-$HT_7$ receptor subtype were collected in an assay buffer (50 mM Tris-HCl, pH 7.4, containing 10 nM $MgCl_2$, 0.2 mM EDTA, 0.001% pargyline and 0.1% ascorbic acid) and homogenized with a Potter type homogenizer. Then the membrane fraction was subjected to 20 minutes of centrifugation at 39,000 g and at 4° C. The thus obtained pellet was re-suspended in 1 ml (per cells per one culture dish of 10 cm in diameter) of the assay buffer and homogenized again. This test was carried out on 1 nM in final concentration of [$^3$H]-5-CT (carboxamide triptamine) and 1 to 1, 000 nM of the compounds of Examples 1 to 90 represented by the general formula (I). A 100 μl of the membrane fraction was added to the reaction tube, final assay volume was adjusted to 500 μl, and the reaction was carried out by incubating the medium at 37° C. for 15 minutes. The incubation was terminated by quickly filtering the reaction system on a GF/B filter which was subsequently washed with 6 ml of cold 50 mM Tris-HCl (pH 7.4). Radioactivity was measured using Packard liquid scintillation counter. Non-specific binding was determined by 10 μM metergoline, and the specific binding was calculated based on the difference. $IC_{50}$ value of each compound was determined by non-linear least square regression analysis, and dissociation constant Ki was calculated from the value.

It was confirmed by this test that the Ki value of the compounds of the present invention represented by the formula (I) for the $5\text{-}HT_7$ receptor was mostly within the range of from 0.001 μM to 1 μM.

TEST EXAMPLE 2

Binding Affinity for $5\text{-}HT_2$ receptor

Rat cerebral cortex was homogenized in 10 volumes of 0.32 M sucrose solution and centrifuged for 10 minutes at 900×g, and the resulting supernatant fluid was again centrifuged for 20 minutes at 11,500×g. The thus obtained precipitate was re-suspended in 500 mM Tris-HCl (pH 7.4) buffer and centrifuged for 20 minutes at 39,900×g, and the thus obtained precipitate was used as P2 fraction. The P2 fraction was incubated at 37° C. for 15 minutes in 50 mM Tris-HCl (pH 7.4) buffer containing 1 nM of [$^3$H] ketanserin and each of the compounds of the present invention and then filtered after the reaction using Whatman GF/B glass filter. The $^3$H radioactivity on the filter was measured using a liquid scintillation counter. Non-specific binding was determined in the presence of 10 μM ketanserin, and the specific binding was calculated based on the difference. $IC_{50}$ value of each compound was determined by non-linear least square regression analysis, and dissociation constant Ki was calculated from the value. The dissociation constant of $5\text{-}HT_2$ obtained by this test, dissociation constant of $5\text{-}HT_7$ obtained in Test Example 1 and their ratio are shown in the following table. As is evident from the results shown in the following table, compounds of the present invention show their affinity for $5\text{-}HT_2$ receptor too, but they bind more selectively to $5\text{-}HT_7$ receptor.

TABLE

| Compound Name | Ki (nM) of $5\text{-}HT_2$ | Ki (nM) of $5\text{-}HT_7$ | $5\text{-}HT_2/5\text{-}HT_7$ |
|---|---|---|---|
| Compound 5 | 61 | 8.9 | 7.0 |
| Compound 56 | 414 | 27 | 15.0 |
| Compound 87 | 120 | 11 | 11.0 |

INDUSTRIAL APPLICABILITY

Compounds of the present invention bind more selectively to a serotonin receptor subtype $5\text{-}HT_7$ receptor. In consequence, the compounds represented by the formula (I) of the present invention and their pharmaceutically acceptable salts are useful as pharmaceutical compositions for the prevention or treatment of mental and nervous diseases of the central nervous system, including manic-depressive psychosis, anxiety and schizophrenia, in which serotonin receptors are concerned.

What is claimed is:

1. A compound represented by formula (I):

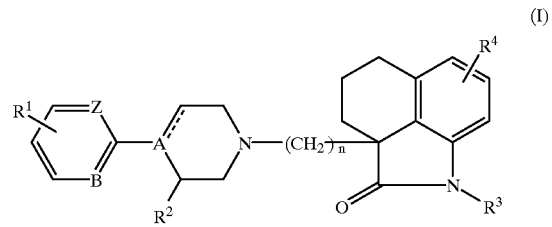

wherein A represents N, CH, C having a double bond or $CR^5$; each of B and Z independently represents N or $CR^1$, with the proviso that A is N when B and/or Z is N; $R^1$ represents a hydrogen atom, a halogen atom, a lower alkyl group, a cyano group, a trihalomethyl group, a hydroxy group, an alkoxy group, an alkylthio group, an alkylsulfinyl group, an alkylsulfonyl group, an alkoxycarbonyl group, a sulfamoyl group, an amino group, a substituted amino group, a carbamoyl group, an alkylcarbamoyl group, an acyl group or a carboxy group; $R^2$ represents a hydrogen atom or a lower alkyl group; $R^3$ represents a hydrogen atom, a lower alkyl group or an aralkyl group; $R^4$ represents a hydrogen atom, a halogen atom, a lower alkyl group, a hydroxy group, an alkoxy group, an acyl, an alkoxycarbonyl group, a nitro group, an amino group, a substituted amino group, a carbamoyl group, an alkylcarbamoyl group or an acyloxy group; $R^5$ represents a lower alkyl group, a cyano group, a carbamoyl group, a carboxy group, an acyl group, an acyloxy group, an alkoxy group, an alkoxycarbonyl group, a trihalomethyl group or a hydroxy group; and n is an integer of 2 to 6 or a pharmaceutically acceptable salt thereof.

2. A compound according to claim 1, wherein B and Z represent CH; and A represents N or CH; or a pharmaceutically acceptable salt thereof.

3. A compound according to claim 1, wherein A represents C having a double bond and $R^2$ represents a hydrogen atom; or a pharmaceutically acceptable salt thereof.

4. A compound according to claim 1, wherein B and Z represent CH; and A represents $CR^5$ and $R^2$ represents a hydrogen atom; or a pharmaceutically acceptable salt thereof.

5. A compound according to claim 1, wherein B and A represent N; and $R^2$ represents a hydrogen atom; or a pharmaceutically acceptable salt thereof.

6. A pharmaceutical composition which contains the compound of any one of claims 1 and 2–5; or a pharmaceutically acceptable salt thereof.

7. A method for treating a disease or disorder selected from the group consisting of: manic-depressive psychosis, gastrointestinal disease, cardiovascular disease and sleep disorders, said method comprising administering a daily dose of the pharmaceutical composition of claim 6 to a human or animal who would benefit from said treating.

8. A compound represented by formula (a-1):

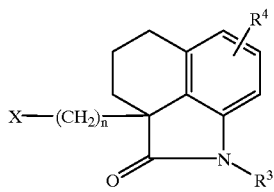

wherein X represents a halogen atom, a methanesulfonyloxy group, an ethanesulfonyloxy, a benzenesulfonyloxy group or a p-toluenesulfonyloxy group; and $R^3$ represents a hydrogen atom, a lower alkyl group or an aralkyl group; $R^4$ represents a hydrogen atom, a halogen atom, a lower alkyl group, a hydroxy group, an alkoxy group, an acyl group, an alkoxycarbonyl group, a nitro group, an amino group, a substituted amino group, a carbamoyl group, an alkylcarbamoyl group or an acyloxy group; and n is an integer of 2 to 6.

9. A compound according to claim 8 wherein X represents a halogen atom.

10. A compound according to claim 8 wherein X represents a benzenesulfonyloxy group or a p-toluenesulfonyloxy group.

11. A compound according to claim 8 wherein X represents a methanesulfonyloxy group or an ethanesulfonyloxy group.

* * * * *